(12) United States Patent
Olsen et al.

(10) Patent No.: US 6,201,110 B1
(45) Date of Patent: *Mar. 13, 2001

(54) POLYPEPTIDE WITH REDUCED RESPIRATORY ALLERGENICITY

(75) Inventors: Arne Agerlin Olsen, Virum; Lars Bo Hansen, Herlev; Thomas Christian Beck, Birkerød, all of (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 09/610,751

(22) Filed: Jul. 6, 2000

Related U.S. Application Data

(63) Continuation of application No. 09/405,311, filed on Sep. 20, 1999, now Pat. No. 6,114,509, which is a continuation of application No. 09/150,891, filed on Sep. 10, 1998, now Pat. No. 5,981,718, which is a continuation of application No. 08/836,293, filed on May 12, 1997, now Pat. No. 5,856,451, which is a continuation of application No. PCT/DK95/00497, filed on Dec. 7, 1994.

(30) Foreign Application Priority Data

| Dec. 7, 1994 | (DK) | 1395/94 |
|---|---|---|
| Dec. 7, 1994 | (DK) | 1396/94 |
| Dec. 7, 1994 | (DK) | 1397/94 |
| Dec. 7, 1994 | (DK) | 1398/94 |
| Dec. 7, 1994 | (DK) | 1399/94 |
| Dec. 7, 1994 | (DK) | 1400/94 |
| Dec. 7, 1994 | (DK) | 1401/94 |

(51) Int. Cl.$^7$ ................................. C07K 1/10
(52) U.S. Cl. ................ 530/402; 530/350; 530/403; 435/189; 435/190
(58) Field of Search ................... 530/402, 350, 530/403; 435/189, 190

(56) References Cited

U.S. PATENT DOCUMENTS

| 4,179,337 | 12/1979 | Davis et al. | 435/181 |
|---|---|---|---|
| 5,080,891 | 1/1992 | Saifer et al. | 424/78 |
| 5,133,968 | 7/1992 | Nakayama et al. | 424/401 |
| 5,230,891 | 7/1993 | Nakayama et al. | 424/401 |

FOREIGN PATENT DOCUMENTS

| 0 223 221 | 11/1986 | (EP) . |
|---|---|---|
| 0 256 127 | 7/1987 | (EP) . |
| WO 93/15189 | 8/1993 | (WO) . |
| WO 93/20838 | 10/1993 | (WO) . |
| WO 94/10191 | 5/1994 | (WO) . |

*Primary Examiner*—Chhaya D. Sayala
(74) *Attorney, Agent, or Firm*—Elias J. Lambiris, Esq.

(57) ABSTRACT

The invention relates to modified polypeptides with reduced respiratory allergenicity comprising a parent polypeptide with a molecular weight from between 10 kDa and 100 kDa conjugated to a polymer with a molecular weight ($M_r$) in the range of 1 kDa and 60 kDa. The modified polypeptide are produced using a process including the step of conjugating from 1 to 30 polymer molecules with the parent polypeptide. Further the invention relates to compositions comprising said polypeptides and further ingredients normally used in e.g. detergents, including dishwashing detergents and soap bars, household article, agrochemicals, personal care products, cosmetics, toiletries, oral and dermal pharmaceuticals, composition for treating textiles, and compositions used for manufacturing food and feed. Finally the invention is directed to uses of polypeptides with reduced allergenicity or compositions thereof for reducing the allergenicity of products for a vast number of industrial applications.

14 Claims, 5 Drawing Sheets

POLYPEPTIDE WITH REDUCED RESPIRATORY ALLERGENICITY

CROSS-REFERENCE TO RELATED APPLICATIONS

This application is a continuation of application Ser. No. 09/405,311 filed Sep. 20, 1999, now U.S. Pat. No. 6,114,509 which is a continuation of 09/150,891, filed Sep. 10, 1998, (now U.S. Pat. No. 5,981,718), which is a continuation of application Ser. No. 08/836,293 filed May 12, 1997 (now U.S. Pat. No. 5,856,451), which is a continuation of PCT/DK95/00497, filed Dec. 7, 1995, and claims priority under 35 U.S.C. 119 of Danish applications serial numbers 1395/94, 1396/94, 1397/94, 1398/94, 1399/94, 1400/94, and 1401/94, all of which were filed on Dec. 7, 1994, the contents of which are hereby incorporated by reference.

FIELD OF THE INVENTION

The invention relates to modified polypeptides, such as proteins or enzymes, with reduced allergenicity. Further the invention is directed towards a process for producing said modified polypeptides with reduced allergenicity, and also compositions thereof. Finally the invention relates to uses of said modified polypeptides with reduced allergenicity or compositions thereof.

BACKGROUND OF THE INVENTION

An increasing number of polypeptides, including proteins and enzymes, are being produced industrially by microorganisms for use in industry, household, food/feed, cosmetics or medicine etc. Said polypeptides may under certain circumstances inflict a potential risk to especially employees handling the manufacturing of products containing polypeptides, and also to some extent to users of these products, such as hairdressers, and end-users of cosmetic and toiletry products etc.

This potential risk need to be controlled and/or limited.

Allergenicity of Polypeptides

In general polypeptides are potential antigens toward which the human immune system can produce specific antibodies upon exposure. This process is known as "immunization" when a clinical beneficial response is obtained whereas the term "sensitization" is applied when the response leads to hypersensitivity. During the primary exposure clonal selection and expansion of the specific B-cell clones are initiated, meaning that a protective or allergic response will only be a clinically manifest upon following exposures. The allergic reaction can be defined as an pathological immune response elicited by otherwise unharmful agents in low concentrations.

The process of sensitisation leading to type IV hypersensitivity are characterized by the formation of specific IgE antibodies. At present, the mechanism controlling the subclass shifting are not fully understood.

IgE secreted from activated B-cells can attach to Fcε receptors located on the surface of mast cells and basophil granulocytes, which contain numerous cytoplasmic granules packed with chemical mediators e.g. histamine (J. Klein, "Immunology", Blackwell Sci. Pub., London, 1990; E. Benjamini & S. Leskowitz, "Immunology", Wiley-Liss, N.Y. 1991).

In atopic individuals each of these cells can have a high number of IgE molecules bound to its surface, where they can remain available to interact with allergens for weeks. Upon contact with an allergen the surface bound IgE cross-binds the allergen, leading to the release of cytoplasmic granules into the proximity of the cell; thereby causing the inflammatoric allergic reaction.

The role of IgE has been shown to relate to natural immunologic defence systems towards parasitic worms infections and the development of allergies has been suggested to be an unfortunate by-product of this defence system.

The natural allergens causing IgE mediated hypersensitivity can be classified according to their way of exposure: Inhalant allergens (pollens, dust mites etc.), Ingested allergens (milk, eggs etc.); Contact allergens (e.g. from latex) and allergens from stinging insects (e.g. bees, fire ants etc.). The aero-allergens represents clinically by far the largest group, stressing an area of high potential risk for the industrial polypeptides.

Testing for allergy can either be performed as in vivo provocation, most commonly skin prick testing of by a number of in vitro assays, primarily based an IgE levels in pheriperal blood. In spite of great efforts in the latter area the most reliable way to diagnose allergy is still the in vivo challenging, which again has different levels of sensitivity depending on the selected target organ.

For instance, intranasal challenge with allergenic proteins can provoke an allergic response even though skin tests and radioallergosorbent test (RAST) for specific serum IgE are negative (Ivan Roitt, "Essential Immunology", fifth edition, p. 152 and p. 240, 1984).

Reduction of Allergenicity of Polypeptides

Presently, the generation of allergic responses to industrial polypeptides are avoided by immobilizing, granulating, coating or dissolving the products, especially to avoid the formation of airborne material. Anyhow, these methods still represent a risk of dust or aerosol formation during handling and processing, with the subsequent risk of allergic sensitisation.

There will anyhow still be a risk of having polypeptide dust or dissolved polypeptide in aerosol form. Therefore some release of enzymes can occur leading to a possible sensitisation and subsequent allergic response.

Another way of diminishing the problem has been to select polypeptides of human origin for production, e.g. in bacteria, fungi, yeast, or mammalian cell cultures. This may alleviate some problems for humans, but not for animals. Furthermore, it will in many cases not be possible to find polypeptides of human origin with the desired properties, wherefore other origin has to be considered. This can be either human polypeptides that are altered in one or more positions in the molecule, giving the performance that is desired. It might also be molecules from other species, including bacteria, mold etc. All the latter groups of products will have potency for immune stimulation in mammalians.

A further proposition for decreasing allergenicity has been to reduce the size of the protein molecules (see e.g. JP Patent Publication No. 4,112,753, or Research Disclosure No. 335,102). This is, however, a solution that is only available when the activity of the protein is- without importance, or in such rare cases, where the activity of the protein is retained in spite of a breakdown of the protein.

The application of protein engineering has been suggested to reduce the allergenicity of proteins through epitope mapping and subsequent change of the allergenic epitopes (see WO 92/10755 (Novo Nordisk A/S). This procedure usually requires a large investment in work and development.

In the medicinal field suggestions have been made of diminishing the immunogenicity of polypeptides through the attachment of polymer molecules to the polypeptide. This usually has the effect of interfering with the interactions of the polypeptide with other macromolecular structures. Such a conjugate may also exhibit novel-properties: e.g. EP 38 154 (Beecham Group Ltd.) discloses conjugates of allergens with polysarcosine which have immunosuppressive properties.

U.S. Pat. No. 4,179,337 (Davis et al.) concerns non-immunogenic polypeptides, such as enzymes and peptide hormones coupled to polyethylene glycol (PEG) or polypropylene glycol. Between 10 and 100 moles of polymer are used per mole polypeptide and at: least 15% of the physiological activity is maintained. In addition the clearance time in circulation is prolonged, due to the increased size of the PEG-conjugate of the polypeptides in question. The protected polypeptide is injected in an aqueous solution into the mammalian circulatory system or intramuscular. The immunogenicity is assessed from intradermal injection tests.

U.S. Pat. No. 4,179,337 concerns therapeutic applications and the retaining of the corresponding physiological activity. In the context of therapeutic applications it is important to limit the risk of inflicting immunological responses caused by exposure of the allergens intradermally, intravenously or subcutaneously. However controlling respiratory allergens are of no importance. Furthermore the relative amount of polymer necessary to conjugate the polypeptides makes the method expensive.

WO 93/15189 (Veronese et al.) concerns a method to maintain the activity in polyethylene glycol-modified proteolytic enzymes by linking the proteolytic enzyme to a macromolecularized inhibitor. The conjugates are intended for medical applications.

It has been found that the attachment of polypeptides to polymers in general has the effect of reducing the activity of the polypeptide or-interfering with the interaction between the polypeptide and its substrate. EP 183 503 (Beecham Group PLC) discloses a development of the above concept by providing conjugates comprising pharmaceutically useful proteins linked to at least one water-soluble polymer by means of a reversible linking group.

GB patent no. 1,183,257 (Crook et al.) describes chemistry for conjugation of enzymes to polysaccharides via a triazine ring.

EP 471 125 (Kanebo, LTD.) describes a modified protease linked to a polysaccharide via a triazine ring leading to a suppressing effect on antigenicity and dermal hypersensitivity. The employed polysaccharide has an average molecular weight not less than 10 kDa. The modification rate for surface amino acid groups in the modified protease is not less that 30%.

In general it is believed that allergens, entering the respiratory tract, must have a molecular weight below about 100 kDa in order to penetrate the plasma membrane and cause allergic reactions.

Folkeson et al., Acta Physiol. Scand, 139, p. 437–354, 19913, showed that there is an inverse relationship between the molecular weight of an instilled protein marker and the transferred amount (bioavailability) via the respiratory tract to the blood stream.

WO 94/10191. (Novo Nordisk A/S) discloses a process for production of low allergenic protein, wherein the monomeric parent protein molecules are linked together to form an oligomer. This is done e.g.. by using a linker or spacer molecule or by linking the monomeric molecules together by peptide bonds between the C-terminal of the first monomer and the N-terminal of the second monomer.

EP 215 662 (Hasda, Hiroshi) concerns a modified or unmodified protease derived from microorganisms for use in medicaments such as anti-tumour agent. It is suggested that the modification of the protease may be carried out by e.g. coupling with a saccharide, introduction of a hydrophobic polymeric group, conjugation with a low molecular weight anti-tumour agent of a molecular weight less than 2 kDa.

Activation of Polymers

Methods and chemistry for activation of polymers as well as for conjugation of proteins are intensively described in the literature. Commonly used methods for activation of insoluble polymers include activation of functional groups with cyanogen bromide, periodate, glutaraldehyde, biepoxides, epichlorohydrin, divinylsulfone, carbodiimide, sulfonyl halides, trichlorotriazine etc. (see R. F. Taylor, (1991), "Protein immobilisation. Fundamental and applications", Marcel Dekker, N.Y.; S. S. Wong, (1992), "Chemistry of Protein Conjugation and Crosslinking", CRC Press, Boca Raton; G. T. Hermanson et al., (1993), "Immobilized Affinity Ligand Techniques", Academic Press, N.Y.). Some of the methods concern activation of insoluble polymers but are also applicable to activation of soluble polymers e.g. periodate, trichloratriazine, sulfanylhalides, divinylsulfone, carbodiimide etc. The functional groups being amino, hydroxyl, thiol carboxyl, aldehyde or sulfydryl on the polymer and the chosen attachment group on the protein must be considered in choosing the activation and conjugation chemistry which normally consist of i) activation of polymer, ii) conjugation, and iii) blocking of residual active groups.

Several reviews and monographs (Harris, (1985), JMS-REV. Macronol. Chem. Phys. C25, 325–373; Scouten, (1987), Methods in Enzymology vol. 135, Mosbach, K., Ed., Academic Press: Orlando, 30–65; Wong et al., (1992), Enzyme Microb. Technol., 14, 866–874; Delgado et al., (1992), Critical Reviews in Therapeutic Drug Carrier Systems, 9, 249–304; Zalipsky, (1995), Bioconjugate Chem.,; 6, 150–165) have been made concerning the synthesis of activated polyethylene glycols (PEGs).

Methods for activation of polymers can also be found in WO 94/17039, U.S. Pat. No. 5,324,844, WO 94/18247, WO 94/04193, U.S. Pat. No. 5,219,564, U.S. Pat. No. 5,122,614, WO 90/13540 (Enzon), and U.S. Pat. No. 5,281,698 (Cetus), and more WO 93/15189 (Veronese) and for conjugation between activated polymers and enzymes e.g. Coagulation Factor VIII (WO 94/15625), haemoglobin (WO 94/09027), oxygen carrying molecule (U.S. Pat. No. 4,412,989), ribonuclease and superoxide dismutase (Veronese at al., App. Biochem. Biotech., 11, p. 141–45, 1985).

The Object of Prior Art

The relevant prior art concern reducing the immunological response or hypersensitivity (allergy) of polypeptides, proteins and/or enzymes in applications for therapeutic purposes, which is relevant when presenting the allergens intradermally, intravenously or subcutaneously. However prior art do not concern presentation of allergens in industrial applications, which potentially may inflict allergy when inhaled, or in applications, where the end-user may be exposed to polypeptides, for instance, in the use of detergents, cleaning preparations, toiletries and other Personal Care products.

It would therefore be desirable to be able to provide polypeptides, proteins and/or enzymes for non-therapeutic industrial applications with a reduced allergic response when inhaled, and which polypeptides substantially maintain their catalytic activity.

SUMMARY OF THE INVENTION

The present inventors have now surprisingly provided modified polypeptides with reduced allergenicity substantially maintaining the catalytic activity.

First of all the invention relates to modified polypeptide with reduced allergenicity comprising a parent polypeptide with a molecular weight of between 10 kDa and 100 kDa conjugated to a polymer with a molecular weight in the range of 1 kDa and 60 kDa.

In a preferred embodiment of the invention the polypeptide is a protein or an enzyme.

The invention is also directed towards a process for producing said polypeptide with reduced allergenicity comprising the step of conjugating from 1 to 30 polymer molecules to a parent polypeptide.

Further the invention provides compositions comprising said polypeptide and/or other enzymes/polypeptides and/or ingredients normally used in e.g. detergents, including dishwashing detergents and soap bars, household articles, agrochemicals, personal care products, including cleaning preparations e.g. for contact lenses, cosmetics, toiletries, oral and dermal pharmaceuticals, composition for treating textiles, and compositions used for manufacturing food, e.g. for baking, and feed.

Finally the invention relates to uses of polypeptides, proteins or enzymes with reduced allergenicity or compositions thereof for a vast number of industrial applications.

BRIEF DESCRIPTION OF THE INVENTION

DETAILED DESCRIPTION OF THE INVENTION

Figure 1:
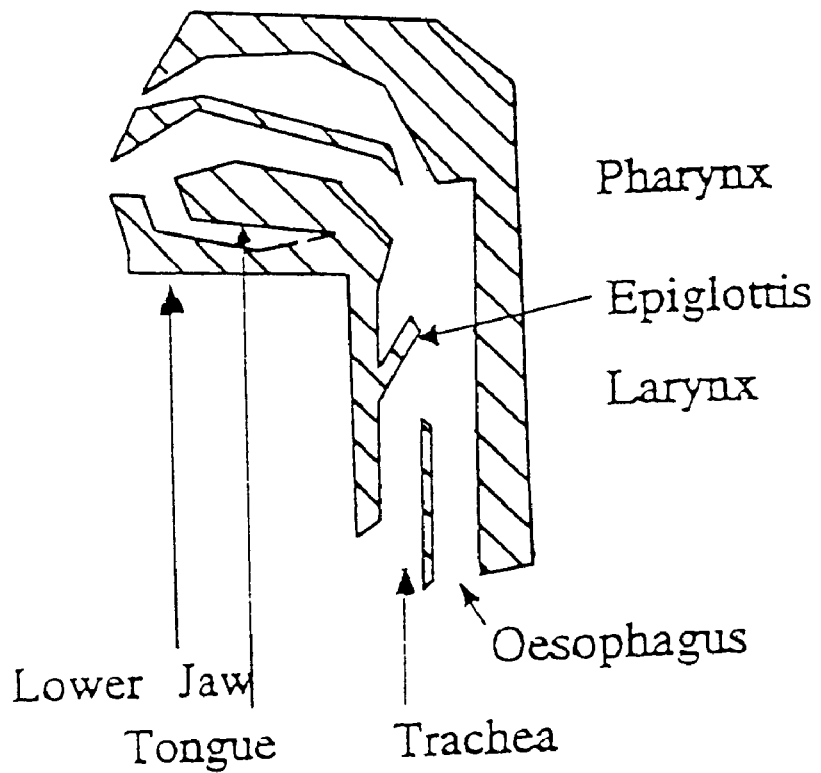
FIG. 1 shows a sectional view of a rat to be intratracaeally exposed to enzymes.
Figure 2:
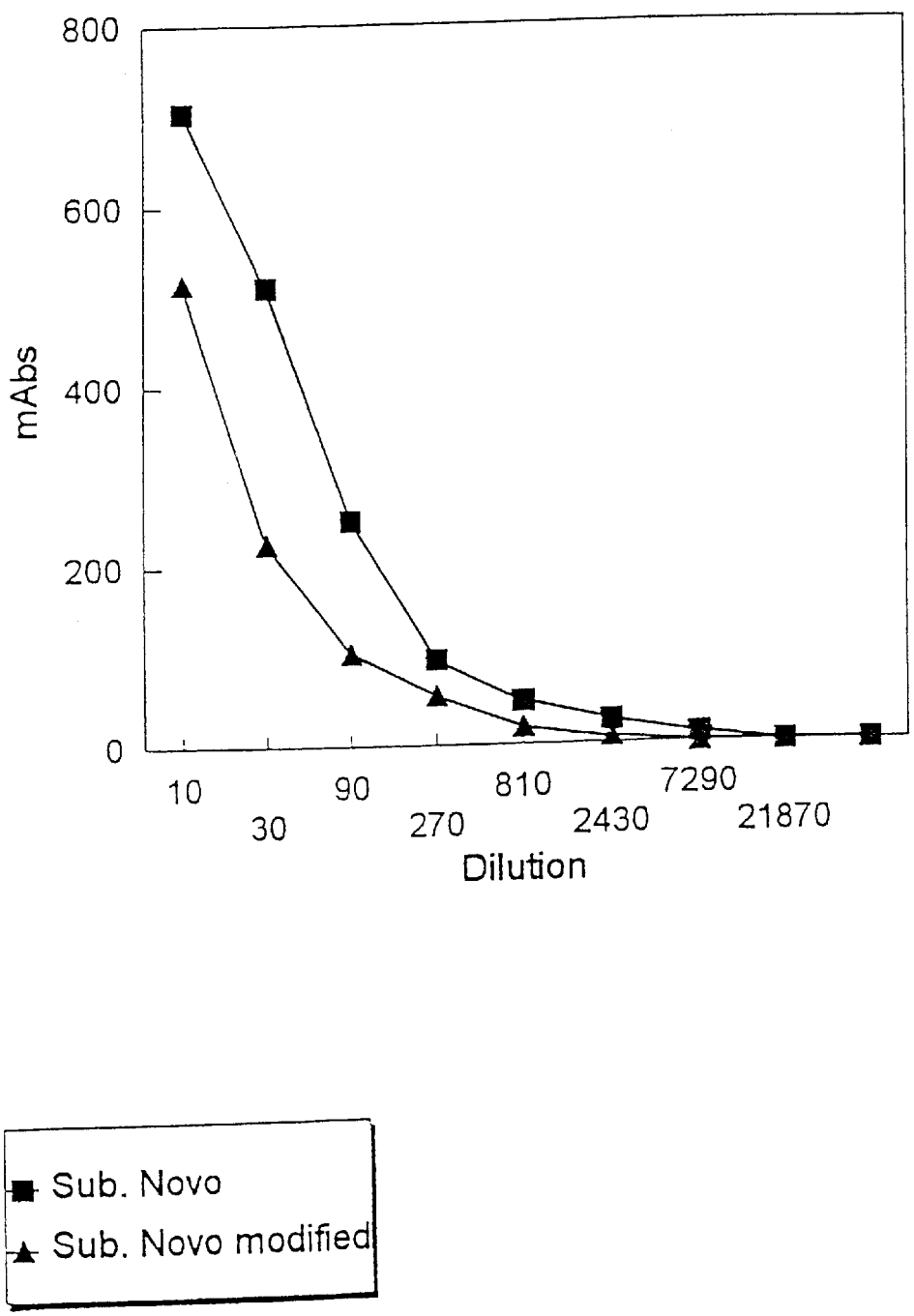
FIG. 2 shows the specific IgE response in Brown Norway Rats sera to modified Subtilisin Novo and parent Subtilisin Novo.
Figure 3:
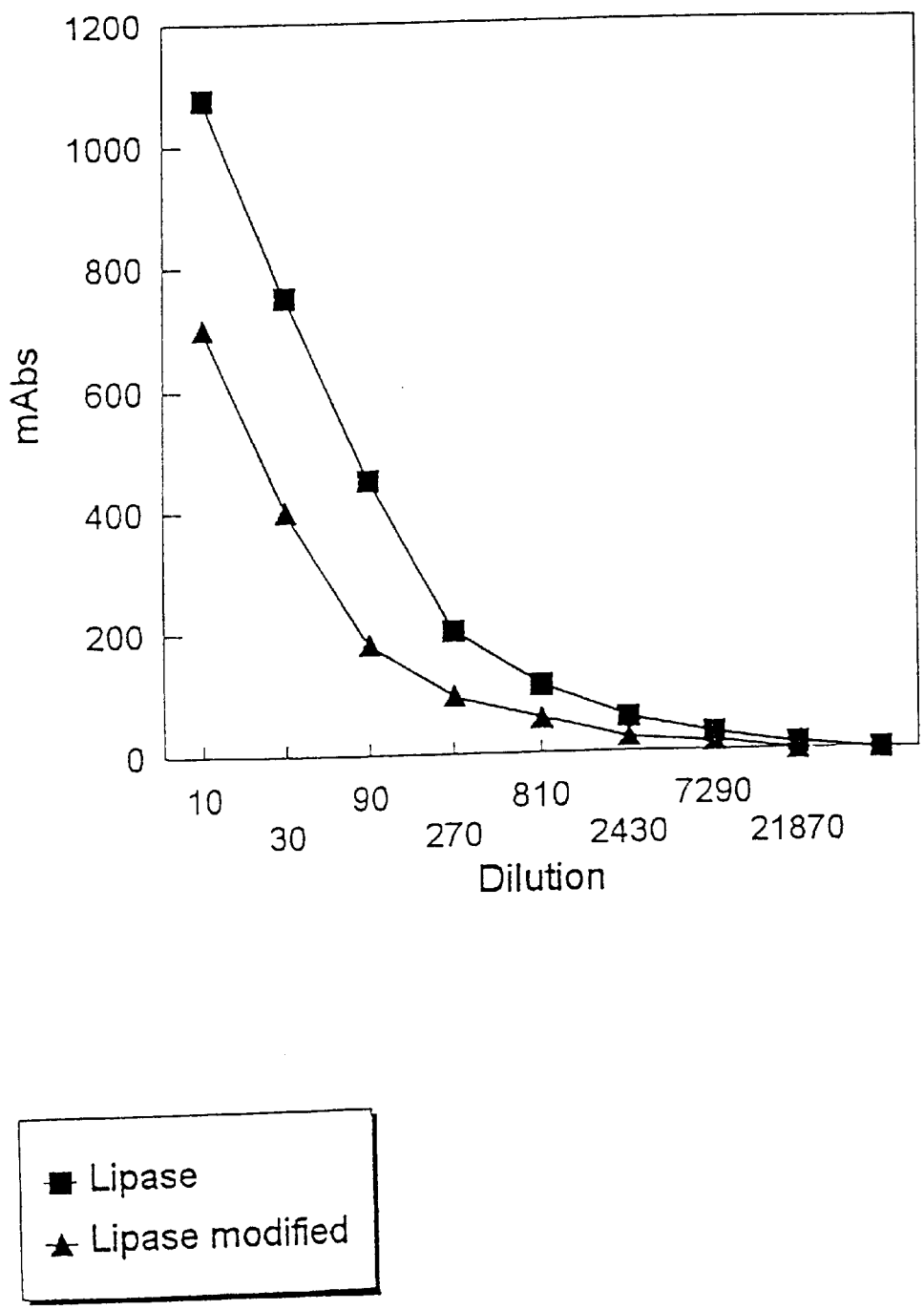
FIG. 3 shows the specific IgE response in Brown Norway Rats sera to modified Lipolase® and parent Lipolase®.
Figure 4:
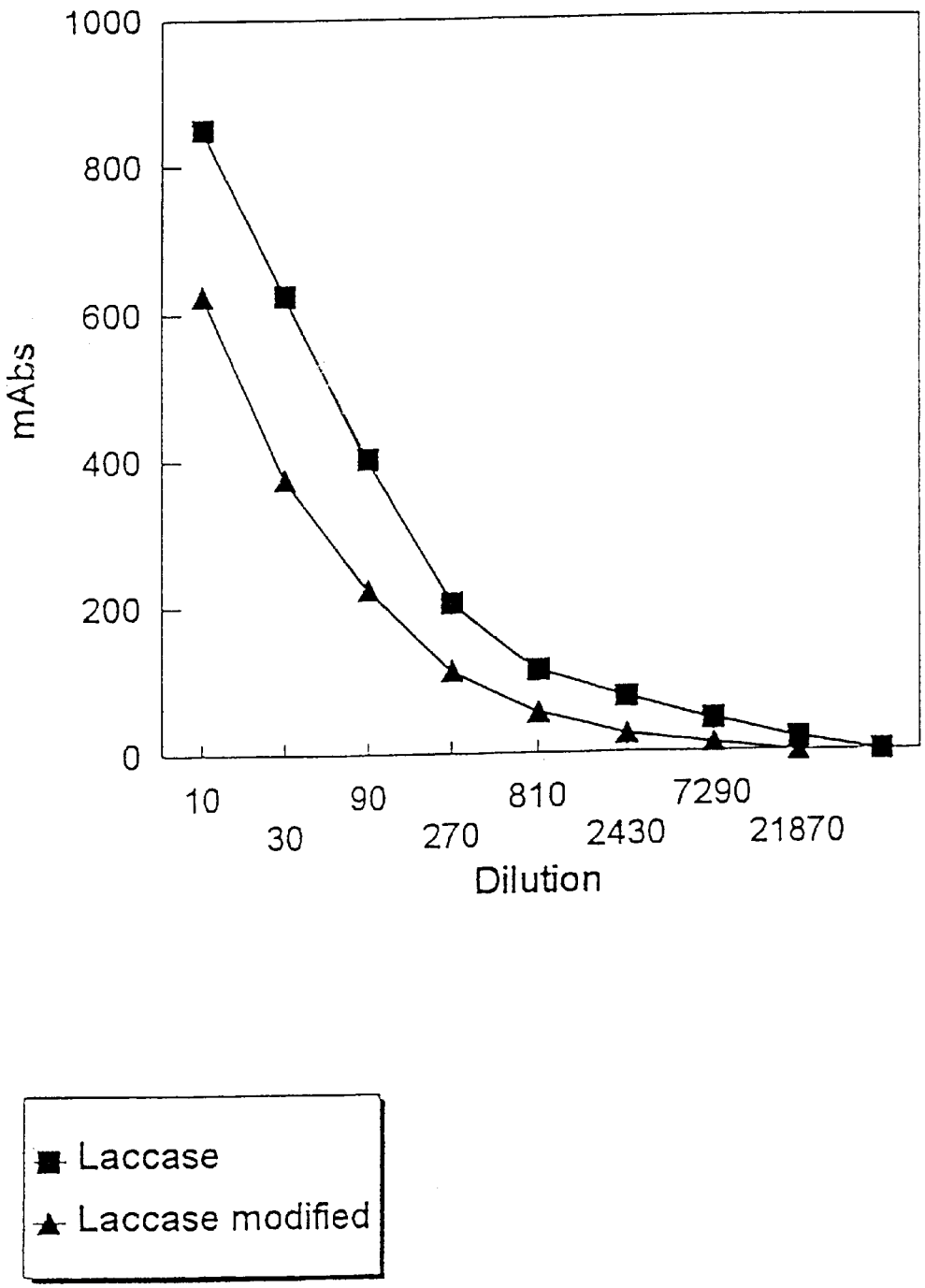
FIG. 4 shows the specific IgE response in Brown Norway Rats sera to modified Laccase and parent Laccase.
Figure 5:
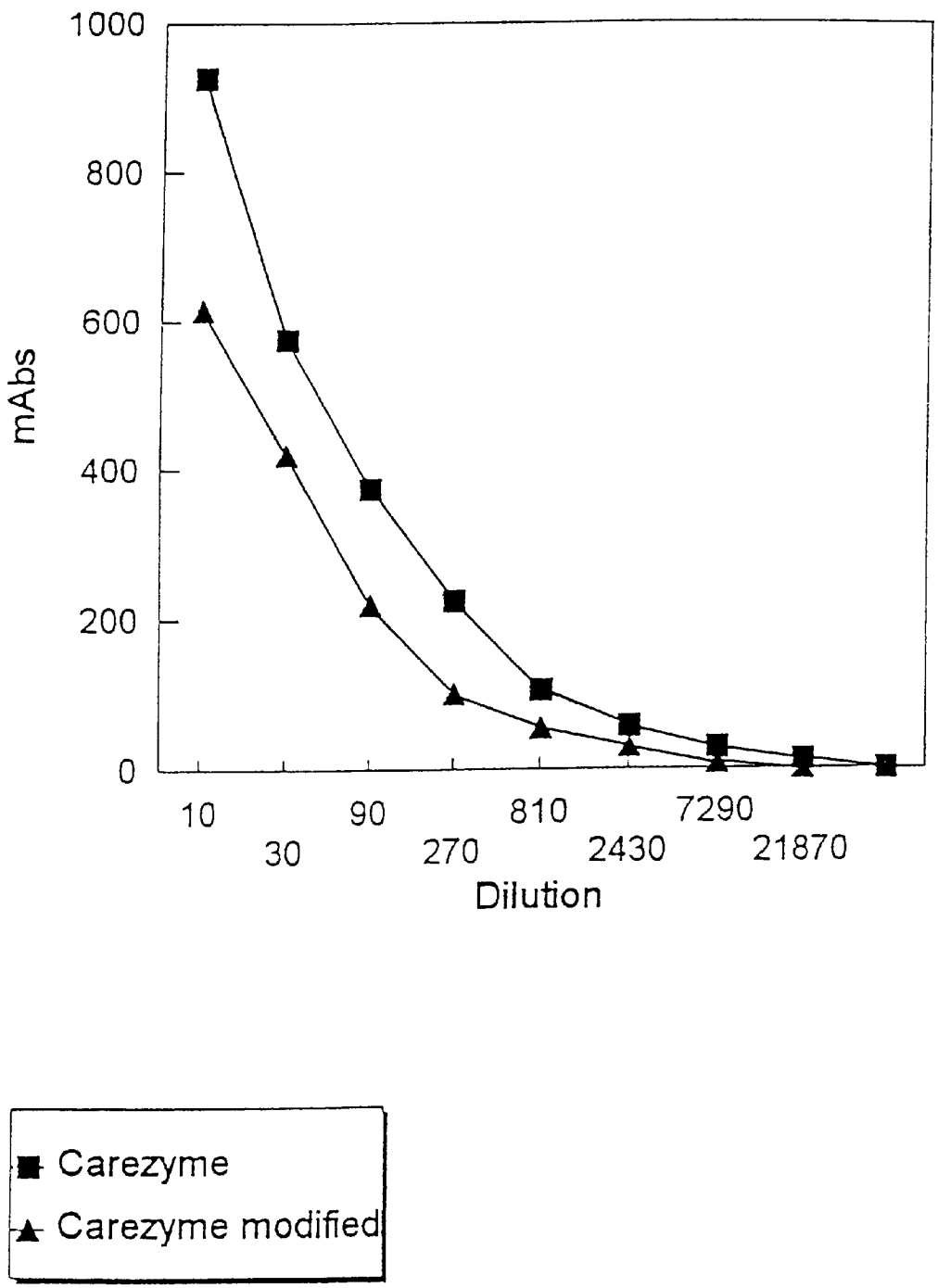
FIG. 5 shows the specific IgE-response in Brown Norway Rats sera to modified Carezyme® and parent Carezyme®.

The present inventors have now surprisingly succeeded in providing modified polypeptides with reduced allergenicity, wherein the catalytic activity is at least substantially maintained.

These modified polypeptides with reduced allergenicity according to the invention solve some of the previously mentioned problems that allergens may inflict when inhaled, within a number of non-therapeutic applications.

Regarding non-therapeutic applications it must be emphasized that it is mainly inhalation of the allergens that may inflict the risk of allergic responses.

Therefore, it is to be understood that one of the crucial advantages of the invention is that the inventors have solved one of the major problems of polypeptides within a vast number of industrial applications, as inhalation, including intratracheal and intranasal presentation of allergens is the main problem in the context of allergenicity. In contrast hereto prior art solutions mainly concern therapeutic applications where intradermally, intravenously or subcutaneously presentation of the allergens are the main problem. Further, inhalation of allergens is a much more sensitive question.

Normally when discussing production for therapeutic purposes it concerns production of enzymes in kilogram scale, while production for industrial purposes concerns production of many 1000 kilograms. Techniques used for therapeutic purposes can not always advantageously be adapted for industrial purposes.

The term "reduced allergenicity" indicates that the amount of produced IgE (in humans, and molecules with comparable effects in specific animals), which can lead to an allergic state, is decreased when inhaling a modified polypeptides of the invention in comparison to the corresponding parent polypeptides.

The terms "immunogen", "antigen" and "allergen" are defined below. The term "immunogen" is the wider term and includes "antigen" and "allergen".

An "immunogen" may be defined as a substance which when introduced into animals, including humans, is capable of stimulating an immunologic response.

The term "antigen" refers to substances which by themselves are capable of generating antibodies when recognized as a non-self molecule.

Further, an "allergen" may be defined as an antigen which may give rise to allergic sensitization or an allergic response by IgE antibodies (in humans, and molecules with comparable effects in animals).

As mentioned above it is, in the context of enzymes including polypeptides for industrial applications, important to distinguish between allergens mediating allergic responses e.g. intradermally, and respiratory allergens causing allergic responses by contact with cell-bound IgE in the respiratory tract, due to the fact that intradermal tests may be negative even though inhalation tests provoke an allergic response.

Therefore, assessment of allergenicity may be made by inhalation tests, comparing the effect of intratracheally (into the trachea) administrated parent polypeptides with the corresponding modified polypeptide with reduced allergenicity according to the invention.

A number of in vitro animal models exist for assessment of the allegenicity of polypeptides. Some of these models give a suitable basis for hazard assessment in man. Suitable models include a guniea pig model and a rat model. These models seek to identify respiratory allergens as a function of elicitation reactions induced in previously sensitised animals. According to these models the alleged allergens are introduced intratracheally into the animals.

A suitable strain of guinea pigs, the Dunkin Hartley strain, do not as humans, produce IgE antibodies in connection with the allergic response. However, they produce another type of antibody the IgG1A and IgG1B (see e.g. Prento, ATLA, 19, p. 8–14, 1991), which are responsible for their allergenic response to inhaled polypeptides including enzymes. Therefore when using the Dunkin Hartley animal model, the relative amount of IgG1A and IgG1B is a measure of the allergenicity level.

A rat strain suitable for intratracheal exposure to polypeptides and enzymes is the Brown Norway strain. The Brown Norway strain produces IgE as the allergic response.

In Example 22 the surprising discoveries of the present invention is disclosed showing that the allergenicity of polypeptides, in the specific cases enzymes, can be reduced by increasing the weight of the enzyme by e.g. coupling a number of polymers to the polypeptide molecule.

Other animals such as rabbits etc. may also be used for comparable studies.

In the first aspect the invention is directed towards modified polypeptides with reduced allergenicity comprising a parent polypeptides with a molecular weight of between 10 kDa and 100 kDa conjugated to a polymer with a molecular weight in the range of 1 kDa and 60 kDa.

The Parent Polypeptide

According to the invention the parent polypeptide may be any polypeptide for industrial applications. This include proteins, enzymes, anti-microbial polypeptides, ligands, inhibitors, enhancers and co-factors.

In a preferred embodiment of the invention parent polypeptide is an enzyme and may be selected from the group of enzymes mentioned in the following.

Parent Proteases

Parent proteases (i.e. enzymes classified under the Enzyme Classification number E.C. 3.4 in accordance with the Recommendations (1992) of the International Union of Biochemistry and Molecular Biology (IUBMB)) include proteases within this group.

Examples include proteases selected from those classified under the Enzyme Classification (E.C.) numbers:

3.4.11 (i.e. so-called aminopeptidases) including 3.4.11.5 (Prolyl aminopeptidase), 3.4.11.9 (X-pro aminopeptidase), 3.4.11.10 (Bacterial leucyl aminopeptidase), 3.4.11.12 (Thermophilic aminopeptidase), 3.4.11.15 (Lysyl aminopeptidase), 3.4.11.17 (Tryptophanyl aminopeptidase), 3.4.11.18 (Methionyl aminopeptidase).

3.4.21 (i.e. so-called serine endopeptidases), including 3.4.21.1 (Chymotrypsin), 3.4.21.4 (Trypsin), 3.4.21.25 (Cucumisin), 3.4.21.32 (Brachyurin), 3.4.21.48 (Cerevisin) and 3.4.21.62 (Subtilisin);

3.4.22 (i.e. so-called cysteine endopeptidases), including 3.4.22.2 (Papain), 3.4.22.3 (Ficain), 3.4.22.6 (Chymopapain), 3.4.22.7 (Asclepain), 3.4.22.14 (Actinidain), 3.4.22.30 (Caricain) and 3.4.22.31 (Ananain);

3.4.23 (i.e. so-called aspartic endopeptidases), including 3.4.23.1 (Pepsin A), 3.4.23.18 (Aspergillopepsin I), 3.4.23.20 (Penicillopepsin) and 3.4.23.25 (Saccharopepsin); and 3.4.24 (i.e. so-called metalloendopeptidases), including 3.4.24.28 (Bacillolysin).

Examples of relevant subtilisins comprise subtilisin BPN', subtilisin amylosacchariticus, subtilisin 168, subtilisin mesentericopeptidase, subtilisin Carlsberg, subtilisin DY, subtilisin 309, subtilisin 147, thermitase, agualysin, Bacillus PB92 protease, proteinase K, Protease TW7, and Protease TW3.

Specific examples of such readily available commercial proteases include Esperasel, Alcalase(, Neutrase®, Dyrazym®, Savinase®, Pyrase®, Pancreatic Trypsin NOVO (PTN), Bio-Feed™ Pro, Clear-Lens Pro (all enzymes available from Novo Nordisk. A/S).

Examples of other commercial proteases include Maxtase®, Maxacal®, Maxapem® marketed by Gist-Brocades N.V., Opticlean® marketed by Solvay et Cie. and Purafectz marketed by Genencor International.

It is to be understood that also protease variants are contemplates as the parent protease. Examples of such protease variants are disclosed in EP 130.756 (Genentech), EP 214.435 (Henkel), WO 87/04461 (Amgen), WO 87/05050 (Genex), EP 251.446 (Genencor), EP 260.105 (Genencor), Thomas et al., (1985), Nature. 318, P. 375–376, Thomas et al., (1987), J. Mol. Biol., 193, pp. 803–813, Russel et al., (1987), Nature, 328, p. 496–500, WO 88/08028 (Genex), WO 88/08033 (Amgen), WO 89/06279 (Nove Nordisk A/S), WO 91/00345 (Nove Nordisk A/S), EP 525 610 (Solvay) and WO 94/02618 (Gist-Brocades N.V.).

The activity of proteases can be determined as described in "Methods of Enzymatic Analysis", third edition, 1984, Verlag Chemie, Weinheim, vol. 5.

Parent Lipases

Parent lipases (i.e. enzymes classified under the Enzyme Classification number E.C. 3.1.1 (Carboxylic Ester Hydrolases) in accordance with the Recommendations (1992) of the International Union of Biochemistry and Molecular Biology (IUBMB)) include lipases within this group.

Examples include lipases selected from those classified under the Enzyme Classification (E.C.) numbers:

3.1.1 (i.e. so-called Carboxylic Ester Hydrolases), including (3.1.1.3) Triacylglycerol lipases, (3.1.1.4.) Phosphorlipase $A_2$.

Examples of lipases include lipases derived from the following microorganisms. The indicated patent publications are incorporated herein by reference:

Humicola, e.g. *H. brevispora, H. lanuginosa, H. brevis* var. *thermoidea* and *H. insolens* (U.S. Pat. No. 4,810,414)

Pseudomonas, e.g. *Ps. fragi, Ps. stutzeri, Ps. cepacia* and *Ps. fluorescens* (WO 89/04361), or *Ps. plantarii* or *Ps. gladioli* (U.S. Pat. No. 4,950,417 (Solvay enzymes)) or *Ps. alcaligenes* and *Ps. pseudoalcaligenes* (EP 218 272) or *Ps. mendocina* (WO 88/09367; U.S. Pat. No. 5,389,536). Fusarium, e.g. *F. oxysporum* (EP 130,064) or *F. solani pisi* (WO 90/09446). Mucor (also called Rhizamucor), e.g. *M. miehei* (EP 238 023). Chromobacterium (especially *C. viscosum*) Aspregillus (especially *A. niger*). Candida, e.g. *C. cylindracea* (also called *C. rugosa*) or *C. antarctica* (WO 88/02775) or *C. antarctica* lipase A or B (WO 94/01541 and WO 89/02916). Geotricum, e.g. *G. candidum* (Schimada et al., (1989), J. Biochem., 106, 383–388) Penicullium, e.g. *P. camembertii* (Yamaguchi et al., (1991), Gene 103, 61–67). Rhizopus, e.g. *R. delemar* (Hass et al., (1991), Gene 109, 107–113) or *R. niveus* (Kugimiya et al., (1992) Biosci. Biotech. Biochem 56, 716–719) or *P. oryzae*. Bacillus, e.g. *B. subtilis* (Dartois et al., (1993) Biochemica et Biophysica acta 1131, 253–260) or *B. stearothermophilus* (JP 64/7744992) or *B. pumilus* (WO 91/16422).

Specific examples of readily available commercial lipases include Lipolase®, Lipolase™ Ultra, Lipozyme®, Palatase®, Novozym® 435, Lecitase® (all available from Novo Nordisk A/S).

Examples of other lipases are Lumafast™, *Ps. mendocian* lipase from Genencor int. Inc.; Lipomax™, *Ps. pseudoalcaligenes* lipase from Gist Brocades/Genencor Int. Inc.; *Fusarium solani* lipase (cutinase), from Unilever; Bacillus sp. lipase from Solvay enzymes. Other lipases are available from other, companies.

It is to be understood that also lipase variants are contemplated as the parent enzyme. Examples of such are described in e.g. WO 93/01285 and WO 95/22615.

The activity of the lipase can be determined as described in "Methods of Enzymatic Analysis", Third Edition, 1984, Verlag, Chemie, Weinhein, vol. 4, or as described in AF 95/5 GB (available on request from Novo Nordisk A/S).

Parent Oxidoreductases

Parent oxidoreductases (i.e. enzymes classified under the Enzyme Classification number E.C. 1 (Oxidoreductases) in accordance with the Recommendations (1992) of the International Union of Biochemistry and Molecular Biology (IUBMB)) include oxidoreductases within this group.

Examples include oxidoreductases selected from those classified under the Enzyme Classification (E.C.) numbers:

Glycerol-3-phosphate dehydrogenase [NAD+] (1.1.1.8), Glycerol-3-phosphate dehydrogenase [NAD(P)+] (1.1.1.94), Glycerol-3-phosphate 1-dehydrogenase [NADP] (1.1.1.94), Glucose oxidase (1.1.3.4), Hexose oxidase (1.1.3.5), Catechol oxidase (1.1.3.14), Bilirubin oxidase (1.3.3.5), Alanine dehydrogenase (1.4.1.1), Glutamate dehydrogenase (1.4.1.2), Glutamate dehydrogenase [NAD (P)+] (1.4.1.3), Glutamate dehydrogenase [NADP+] (1.4.1.4), L-Amino acid dehydrogenase (1.4.1.5), Serine dehydrogenase (1.4.1.7), Valine dehydrogenase [NADP+] (1.4.1.8), Leucine dehydrogenase (1.4.1.9), Glycine dehydrogenase (1.4.1.10), L-Amino-acid oxidase (1.4.3.2.), D-Amino-acid oxidase (1.4.3.3), L-Glutamate oxidase (1.4.3.11), Protein-lysine 6-oxidase (1.4.3.13), L-lysine oxidase (1.4.3.14), L-Aspartate oxidase (1.4.3.16), D-amino-acid dehydrogenase (1.4.99.1), Protein disulfide reductase (1.6.4.4), Thioredoxin reductase (1.6.4.5), Protein disulfide reductase (glutathione) (1.8.4.2), Laccase (1.10.3.2), Catalase (1.11.1.6), Peroxidase (1.11.1.7), Lipoxygenase (1.13.11.12), Superoxide dismutase (1.15.1.1):

Said Glucose oxidases may be derived from *Aspergillus niger*.

Said Laccases may be derived from *Polyporus pinsitus, Myceliophtora thermophila, Coprinus cinereus, Rhizoctonia solani, Rhizoctonia praticola, Scytalidium thermophilum* and *Rhus vernicifera*.

Bilirubin oxidases may be derived from *Myrothechecium verrucaria*.

The Peroxidase may be derived from e.c. Soy bean, Horseradish or *Coprinus cinereus*.

The Protein Disulfide reductase may be any mentioned in any of the DK patent applications no. 768/93, 265/94 and 264/94 (Novo Nordisk A/S), which are herby incorporated as reference, including Protein Disukfide reductases of bovine origin, Protein Disulfide reductases derived from *Aspergillus oryzae* or *Aspergillus niger*, and DsbA or DsbC derived from *Escherichia coli*.

Specific examples of readily available commercial oxidoreductases include Gluzyme™ (enzyme available from Novo Nordisk A/S). However, other oxidoreductases are available from others.

It is to be understood that also variants of oxidoreductases are contemplated as the parent enzyme.

The activity of oxidoreductases can be determined as described in "Methods of Enzymatic Analysis", third edition,. 1984, Verlag Chemie, Weinheim, vol. 3.

Parent Carbohydrases

Parent carboydrases may be defined as all enzymes capable of breaking down carbohydrate chains (e.g. starches) of especially five and six member ring structures (i.e. enzymes classified under the Enzyme Classification number E.C. 3.2 (glycosidases) in accordance with the Recommendations (1992) of the International Union of Biochemistry and Molecular Biology (IUBMB)). Also included in the group of carbohydrases according to the, invention are enzymes capable of isomerizing carbohydrates e.g. six member ring structures, such as D-glucose to e.g. five member ring structures like D-fructose.

Examples include carbohydrases selected from those classified under the Enzyme Classification (E.C.) numbers:

α-amylase (3.2.1.1) β-amylase (3.2.1.2), glucan 1,4-α-glucosidase (3.2.1.3), cellulase (3.2.1.4), endo-1,3(4)-β-glucanase (3.2.1.6), endo-1,4-β-xylanase (3.2.1.8), dextranase (3.2.1.11), chitinase (3.2.1.14), polygalacturonase (3.2.1.15), lysozyme (3.2.1.17), β-glucosidase (3.2.1.21), α-galactosidase (3.2.1.22), β-galactosidase (3.2.1.23), amylo-1,6-glucosidase (3.2.1.33), xylan 1,4-β-xylosidase (3.2.1.37), glucan endo-1,3-β-D-glucosidase (3.2.1.39), α-dextrin endo-1,6-glucosidase (3.2.1.41), sucrose α-glucosidase (3.2.1.48), glucan endo-1,3-α-glucosidase (3.2.1.59), glucan 1,4-β-glucosidase (3.2.1.74), glucan endo-1,6-β-glucosidase (3.2.1.75), arabinan endo-1,5-α-arabinosidase (3.2.1.99), lactase (3.2.1.108), chitonanase (3.2.1.132) and xylose isomerase (5.3.1.5).

Examples of relevant carbohydrases include α-1,3-glucanases derived from *Trichdderma harzianumi*; α-1,6-glucanases derived from a strain of Paecilomyces; β-glucanases derived from *Bacillus subtilis*; β-glucanases derived from *Humicola insolens*; β-glucanases derived from *Aspergillus niger*; β-glucanases derived from a strain of Trichoderma; β-glucanases derived from a strain of *Oerskovia xanthineolytica*; exo-1,4-α-D-glucosidases (glucoamylases) derived from *Aspergillus niger*; α-amylases derived from *Bacillus subtilis*; α-amylases derived from *Bacillus amyloliquefaciens*; α-amylases derived from *Bacillus stearothermophilus*; α-amylases derived from *Aspergillus ozyzae*; α-amylases derived from non-pathogenic microorganisms; α-galactosidases derived from *Aspergillus niger*; Pentosanases, xylanases, cellobiases, cellulases, hemi-cellulases deriver from *Humicola insolens*; cellulases derived from *Trichoderma reesei*; cellulases derived from non-pathogenic mold; pectinases, cellulases, arabinases, hemi-celluloses derived from *Aspergillus niger*; dextranases derived from *Penicillium lilacinum*; endo-glucanase derived from non-pathogenic mold; pullulanases derived from *Bacillus acidopullyticus*; β-galactosidases derived from *Kluyveromyces fragilis*; xylanases derived from *Trichoderma reesei*;

Specific examples of readily available commercial carbohydrases include Alpha-Gal™, Bio-Feed™ Alpha, Bio-Feed™ Beta, Bio-Feed™ Plus, Bio-Feed™ Plus, Novozyme® 188, Carezyme®, Celluclast®, Cellusoft®, Ceremyl®, Citrozym™, Denimax™, Dezyme™, Dextrozyme™, Finizym®, Fungamyl™, Gamanase™, Glucanex®, Lactozym®, Maltogenase™, Pentopan™, Pectinex™, Promozyme®, Pulpzyme™, Novamyl™, Termamyl®, AMG (Amyloglucosidase Novo), Maltogenase®, Sweetzyme®, Aguazym® (all enzymes available from Novo Nordisk A/S). Other carbohydrases are available from other companies.

It is to be understood that also carbohydrase variants are contemplated as the parent enzyme.

The activity of carbohydrases can be determined as described in "Methods of Enzymatic Analysis", third edition, 1984, Verlag Chemie, Weinheim, vol. 4.

Parent Transferases

Parent transferases (i.e. enzymes classified under the Enzyme Classification number E.C. 2 in accordance with the Recommendations (1992) of the International Union of Biochemistry and Molecular Biology (IUBMB)) include transferases within this group.

The parent transferases may be any transferase in the subgroups of transferases: transferases transferring one-carbon groups (E.C. 2.1); transferases transferring aldehyde or residues (E.C 2.2); acyltransferases (E.C. 2.3); glucosyl-transferases (E.C. 2.4); transferases transferring alkyl or aryl groups, other that methyl groups (E.C. 2.5); transferases transferring nitrogeneous groups (2.6).

In a preferred embodiment the parent tranferease is a transglutaminase E.C 2.3.2.13 (Protein-glutamine μ-glutamyltransferase).

Transglutaminases are enzymes capable of catalyzing an acyl transfer reaction in which a gamma-carboxyamide group of a peptide-bound glutamine residue is the acyl donor. Primary amino groups in a variety of compounds may function as acyl acceptors with the subsequent formation of monosubstituted gamma-amides of peptide-bound glutamic acid. When the epsilon-amino group of a lysine residue in a peptide-chain serves as the acyl acceptor, the transferases form intramolecular or intermolecular gamma-glutamyl-epsilon-lysyl crosslinks.

Examples of transglutaminases are described in the pending DK patent application no. 990/94 (Novo Nordisk A/S).

The parent transglutaminase may the of human, aminal (e.g. bovine) or microbially origin.

Examples of such parent transglutaminases are animal derived Transglutaminase, FXIIIa; microbial transglutaminases derived from *Physarum polycephalum* (Klein et al., Journal of Bacteriology, Vol. 174, p. 2599–2605); transglutaminases derived from Streptomyces sp., including , *Streptomyces lavendulae, Streptomyces lydicus* (former *Streptomyces libani*) and Streptoverticillium sp., including *Streptoverticillium mobaraense, Streptoverticillium cinnamoneum*, and *Streptoverticillium griseocarneum* (Motoki et al., U.S. Pat. No. 5,156,956; Andou et al., U.S. Pat. No. 5,252,469; Kaempfer et al., Journal of General Microbiology, Vol. 137, p. 1831–1892; Ochi et al., International Journal of Sytematic Bacteriology, Vol. 44, p. 285–292; Andou et al., U.S. Pat. No. 5,252,469; Williams et al., Journal of General Microbiology, Vol. 129, p. 1743–1813).

It is to be understood that also transferase variants are contemplated as the parent enzyme.

The activity of transglutaminases can be determined as described in "Methods of Enzymatic Analysis", third edition, 1984, Verlag Chemie, Weinheim, vol. 1–10.

Parent Phytases

Parent phytases are included in the group of enzymes classified under the Enzyme Classification number E.C. 3.1.3 (Phosphoric Monoester Hydrolases) in accordance with the Recommendations (1992) of the International Union of Biochemistry and Molecular Biology (IUBMB)).

Phytases are enzymes produced by microorganisms which catalyse the conversion of phytate to inositol and inorganic phosphorus Phytase producing microorganisms comprise bacteria such as *Bacillus subtilis, Bacillus natto* and Pseudomonas; yeasts such as *Saccharomyces cerevisiae*; and fungi such as *Aspergillus niger, Aspergillus ficuum, Aspergillus awamori, Aspergillus oryzae, Aspergillus terreus* or *Aspergillus nidulans*, and various other Aspergillus species)

Examples of parent phytases include phytases selected from those classified under the Enzyme Classification (E.C.) numbers: 3-phytase (3.1.3.8) and 6-phytase (3.1.3.26).

The activity of phytases can be determined as described in "Methods of Enzymatic Analysis", third edition, 1984, Verlag Chemie, Weinheim, vol. 1–10, or may be measured according to the method described in EP-A1-0 420 358, Example 2 A.

Parent Antimicrobial Polypetides

Parent anti-microbial polypeptides may be any polypeptides exhibiting anti-microbial activities, such as anti-fungal, anti-bacterial, and/or anti-insecticidal activity.

Said polypeptides may also exhibit other activities such as enzymatic activity.

Examples of parent anti-microbial polypeptides according to the invention include: fungicidally active polypeptides derived from the mold genus Curvularia described in WO 94/01459 (Novo Nordisk A/S); anti-bacterial polypeptides described in EP 403.458 (Kabigen AB); anti-microbial proteins isolated from the Mirabilis seed, described in WO 92/15691 (Imperial Chem Ind. PLC); anti-bacterial polypeptides isolated from an extract of pig small intestine, described in WO 92/22578 (Boman et al.); polypeptide with yeast lethal action accumulated by yeast of Hansenula spp. as described in JP-60130599; *Phytolacca insularis* antiviral protein, which can be used as an anti-microbial described in U.S. Pat. No. 5,348,865 (Jin Ro LTD.); bacteriolytic enzymes preparations derived from *Nocardiopsis dassonvillei* described in U.S. Pat. No. 5,354,681 (Novo Industri A/S).

Examples of other anti-microbial polypeptides are maganinin, protegrin, defensin, pseudomycin, mutanolysin and N-acetylmuramidase.

Relevant parent polypeptides, proteins or enzymes according to the invention are polypeptides, proteins or enzymes that may cause allergic reactions. These polypeptides, proteins or enzymes are believed to have a molecular weight between 10 kDa and 100 kDa, preferably between 15 kDa and 80 kDa, or between 20 kDa and 70 kDa, or between 25 kDa and 60 kDa, or between 28 kDa and 55 kDa, or between 30 kDa and 50 kDa.

It is within the scope of the present invention to use variants having additional attachment groups, such as amino-groups, in comparison to the parent enzyme. It is advantageous to use such variants as such variants more effectively shield the enzyme towards recognition by the immune system.

The Polymer

Examples of suitable polymers include polymers selected from the group comprising polyalkylene oxides (PAO), such as polyalkylene glycols (PAG), including polyethylene glycols (PEG), methoxypolyethylene glycols (mPEG) and polypropylen glycols, PEG-glycidyl ethers (Epox-PEG), PEG-oxycarbonylimidazole (CDI-PEG), Star-PEGs, Branced PEGs, poly-vinyl alcohol (PVA), poly-carboxylates, poly-(vinylpyrolidone), poly-D,L-amino acids, dextrans including carboxymethyl-dextrans, celluloses, including methylcellulose, carboxymethylcellulose, ethylcellulose, hydroxyethylcellulose carboxyethylcellulose and hydroxypropylcellulose, hydrolysates of chitosan, starches such as hydroxyethyl-straches and hydroxypropyl-starches, glycogen, agaroses and derivates thereof, guar gum, pullulan, inulin, xanthan gum, carrageenin, pectin, alginic acid hydrolysates and bio-polymers.

Star PEGs are multi-armed PEG molecules made by polymerization of ethyl oxide molecules from a crosslinked divinyl benzene core (Gnanou et al., (1988), Makromol. Chem 198, 2885; Rein wt al., (1993), Acta Polymer, 44, 225). Star PEGS and Branced PEGs are available from Shearwater Inc., USA).

Epox-PEGs (or PEG-glycidyl ether) are PEGs with an epoxide as the activated coupling group ar the end. They can undergo reactions/attachment with amino-, hydroxyl- and thiol-groups of proteins /Elling and Kula, (1991), Biotech. Appl. Biochem, 13, 354). Epox-PEGs are available from Shearwater Inc., USA, as e.g. methoxy-PEG-epoxides and PEG-(epoxides)$_2$.

CDI-PEGs (or PEG oxycarbonylimidazole) are PEGs with a carbonylimodazole as the reactive end-group. Said reactive/activated attachment group conjugates with the protein via a urethane linkage (Beauchamp et al., 1993), Anal. Biochem., 131, 125). CDI-PEGs are available from Shearwater Inc., USA, as e.g. methoxy-PEG-CDI and PEG-(CDI)$_2$.

Examples of such suitable readily available polymer products (of which some are activated polymers) include polyethylene glycols (e.g. from Merck) having an average molecular weight of between about 1 kDa and 35 kDa, methoxypolyethylene glycols (e.g. from Sigma) having an average molecular weight of about 5 kDa and dextrans (e.g. from Fluka) having an average molecular weight of between about 1 kDa and 60 kDa and even higher.

Even though all of the above mentioned polymers can be used according to the invention the methoxypolyethylene glycols may advantageously be used. This arise from the fact that methoxyethylene glycols only have one reactive end capable of conjugating with the polypeptide. Consequently, the risk of cross linking is less pronounced. Further, it makes the product more homogeneous and the reaction of the polymer with the polypeptide easier to control.

Polymers having a molecular weight (H) between 1 and 60 kDa may be used according to the invention. Preferred are polymers having a molecular weight ($M_r$) of between 2 kDa and 35 kDa, especially between 2 kDa and 25 kDa, such as about 5 kDa or about 15 kDa.

Note that all polymer molecular weights mentioned in this application are average molecular weights.

In a preferred embodiment of the invention the polymer is a polyethylene glycol (PEG), such as, a methoxypolyethylene glycol (mPEG).

Activation of Polymers

If the polymer to be used for conjugating the polypeptide is not active it must be activated by a suitable method. The methods referred in the "Background of the Invention" section are examples of methods which may be used according to the present invention. However, the most suitable method may differ for molecule to molecule dependent on e.g. available attachment groups on the polypeptide chain.

In the following further methods of suitable polymer activation methods will be described shortly. However, it is to be understood that also other methods can be used.

Coupling polymers to the free acid groups of enzymes can be performed with the aid of diimide and for example amino-PEG or hydrazino-PEG (Pollak et al., (1976), J. Amr. Chem. Soc., 98, 289–291) or diazoacetate/amide (Wong et al., (1992), supra).

Coupling polymers to hydroxy groups are generally very difficult as it must be performed in water. Usually hydrolysis predominates over reaction with hydroxyl groups.

Coupling polymers to free sulfhydryl groups can be reached with special groups like maleimido or the orthopyridyl disulfide. Also vinylsulfone (U.S. Pat. No. 5,414,135, (1995), Snow et al.) has a preference for sulfhydryl groups but is not as selective as the other mentioned.

Accessible arginine residues in the polypeptide chain may be targeted by groups comprising two vicinal carbonyl groups.

Techniques involving coupling electrophilically activated PEGs to the amino groups of lysins can also be useful. Many of the usual leaving groups for alcohols give rise to an amine linkage. For instance, alkyl sulfonates, such as tresylates (Nilsson et al., (1984), Methods in Enzymology vol. 104, Jacoby, W. B., Ed., Academic Press: Orlando, p. 56–66; Nilsson et al., (1987), Methods in Enzymology vol. 135;Mosbach, K., Ed.; Academic Press: Orlando, pp. 65–79; Scouten et al., (1987), Methods in Enzymology vol. 135, Mosbach, K., Ed., Academic Press: Orlando, 1987; pp 79–84; Crossland et al., (1971), J. Amr. Chem. Soc. 1971, 93, pp. 4217–4219), mesylates (Harris, (1985), suera; Harris et al., (1984), J. Polym. Sci. Polym. Chem. Ed. 22, pp 341–352), aryl sulfonates like tosylates, and para-nitrobenzene sulfonates can be used.

Organic sulfonyl chlorides, e.g. Tresyl chloride, effectively converts hydroxy groups in a number of polymers, e.g. PEG, into good leaving groups (sulfonates) that, when reacted with nucleophiles like amino groups in polypeptides allow stable linkages to be formed between polymer and polypeptide. In addition to high conjugation yields, the reaction conditions are in general mild (neutral or slightly alkaline pH, to avoid denaturation and little or no disruption of activity), and satisfy the non-destructive requirements to the polypetide.

Tosylate is more reactive than the mesylate but also more unstable decomposing into PEG, dioxane, and sulfonic acid (Zalipsky, (1995), supra) . Epoxides may also been used for creating amine bonds but are much less reactive than the above mentioned groups.

Converting PEG into a chloroformate with phosgene gives rise to carbamate linkages to lysins. This theme can be played in many variants substituting the chlorine with N-hydroxy succinimide (U.S. Pat. No. 5,122,614, (1992), Zalipsky; Zalipsky et al., (1992), Biotechnol. Appl. Biochem., 15, p. 100–114; Monfardini et al., (1995), Bioconjugate Chem., 6, 62–69, with imidazole (Allen et al., (1991), Carbohydr. Res., 213, pp 309–319), with para-nitrophenol, DMAP (EP 632 082 A1, (1993), Looze, Y.) etc. The derivatives are usually made by reacting the chloroformate with the desired leaving group. All these groups give rise to carbamate linkages to the peptide.

Furthermore, isocyanates and isothiocyanates may be employed yielding ureas and thicureas, respectively.

Amides may be obtained from PEG acids using the same leaving groups as mentioned above and cyclic imid thrones (U.S. Pat. No. 5,349,001, (1994), Greenwald et al.). The reactivity of these compounds are very high but may make the hydrolysis to fast.

PEG succinate made from reaction with succinic anhydride can also be used. The hereby comprised ester group make the conjugate much more susceptible to hydrolysis (U.S. Pat. No. 5,122,614, (1992), Zalipsky). This group may be activated with N-hydroxy succinimide.

Furthermore, a special linker can be introduced. The oldest being cyanuric chloride (Abuchowski et al., (1977), J. Biol. Chem., 252, 3578–3581; U.S. Pat. No. 4,179,337, (1979), Davis, et al.; Shafer et al., (1986), J. Polym. Sci. Polym. Chem. Ed., 24, 375–378.

Coupling of PEG to an aromatic amine followed by diazotation yields a very reactive diazonium salt which in situ can be reacted with a peptide. An amide linkage may also be obtained by reacting an azlactone derivative of PEG (U.S. Pat. No. 5,321,095, (1994), Greenwald, R. B.) thus introducing an additional amide linkage.

As some peptides do not comprise many lysins it may be advantageous to attach more than one PEG to the same lysine. This can be done e.g. by the use of 1,3-diamino-2-propanol.

PEGs may also be attached to the amino-groups of the polypeptide with carbamate linkages (WO 95/11924 Greenwald et al.). Lysine residues may also be used as the backbone.

The Conjugate

According to the invention conjugates of modified polypeptide have a total molecular weight in the range from 5.0 kDa to 500 kDa, preferably 50 kDa to 400, more preferred 50 kDa to 250 kDa, especially 100 kDa to 250 kDa, such as 80 kDa to 200 kDa.

A modified polypeptide according to the invention may demonstrate a high degree of stability.

For most applications, including Personal Care applications, the modified enzymes may advantageously be irreversible conjugated to the polymer, which entails that the product has only negligible tendency to disintegrate, which would lead to the return of conditions that may cause an allergenic state.

However, in certain other cases it is advantageous that the enzymes stay conjugated to the polymer in the production and/or bulk handling phase, but disintegrates later on, when the enzyme do not inflict a risk of exposure to humans or animals.

The disintegration of the conjugated modified polypeptide of the invention may be activated e.g. by physical conditions, such as pH, ionic strength, temperature, reduction or oxidation potential etc. An example of this is disintegration upon dissolving a detergent formulation.

Further, the presence of specific compounds may result in disintegration, e.g. into molecules being less conjugated and/or molecules in the parent form.

Especially in the case where the activity of the polypeptide, protein or enzyme is reduced in the conjugated form, disintegration may be advantageous.

The invention also relates to a process for producing polypeptides with reduced allergenicity comprising the step of conjugating the parent polypeptide with from 1 to 30 polymer molecules, preferably 1 to 25, such as 1 to 10 polymer molecules.

Examples of said polymers which may be used according to the invention are listed above.

Preferably between 1 and 25 polymer molecules are conjugated to each polypeptide molecule. This is less than corresponding prior art techniques. Consequently the expense to polymer is reduced. To some extent it entails that the activity of the polypeptide, protein or enzyme is substantially maintained, as it is to be anticipated that the activity vary inversely with the number and the size of polymer conjugated to the polypeptide chain.

According to the invention more than 5%, in most cases about 20% to 50%, better 50% to 70%, even better between 70% and 80%, up to between 80% and 90% and even up to 100%, of the activity of the polypeptide is maintained.

Composition

The invention also relates to a composition comprising at least one polypeptide, protein or enzyme of the invention.

The composition may further comprise other polypeptides, proteins or enzymes and/or ingredients normally used in e.g. detergents, including soap bars, household articles, agrochemicals, personal care products, such as cleaning preparations e.g. for contact lenses; cosmetics, toiletries, oral and dermal pharmaceuticals, composition use for treating textiles, compositions used for manufacturing food, e.g. baking, and feed etc.

Examples of said polypeptides/proteins/enzymes include enzymes exhibiting protease, lipase, oxidoreductase, carbohydrase, transferase, such as transglutaminase, phytase and/or anti-microbial polypeptide activity. These enzymes may be present as conjugates with reduces activity.

It is also contemplated according to the invention to combine the use of conjugated enzymes with the same activity having different specificity.

Detergent Compositions

If the polypeptide of the invention is an enzyme it may typically be used in detergent composition. It may be included in the detergent composition in the form of a non-dusting granulate, a stabilized liquid, or a protected enzyme. Non-dusting granulates may be produced, e.g., as disclosed in U.S. Pat. No. 4,106,991 and 4,661,452 (both to Novo Industri A/S) and may optionally be coated by methods known in the art. Examples of waxy coating materials are poly(ethylene oxide) products (polyethylene glycol, PEG) with mean molecular weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in patent GB 1483591. Liquid enzyme preparations may, for instance, be stabilized by adding a polyol such as propylene glycol, a sugar or sugar alcohol, lactic acid or boric acid according to established methods. Other enzyme stabilizers are well known in the art. Protected enzymes may be prepared according to the method disclosed in EP 238,216.

The detergent composition may be in any convenient form, e.g. as powder, granules, paste or liquid. A liquid detergent may be aqueous, typically containing up to 70% water and 0–30% organic solvent, or non-aqueous.

The detergent composition comprises one or more surfactants, each of which may be anionic, nonionic, cationic, or zwitterionic. The detergent will usually contain 0–50% of anionic surfactant such as linear alkylbenzenesulfonate (LAS), alpha-olefinsulfonate (AOS), alkyl sulfate (fatty alcohol sulfate) (AS), alcohol ethoxysulfate (AEOS or AES), secondary alkanesulfonates (SAS). alpha-sulfo fatty acid methyl esters, alkyl- or alkenylsuccinic acid, or soap. It may also contain 0–40% of nonionic surfactant such as alcohol ethoxylate (AEO or AE), carboxylated alcohol ethoxylates, nonylphenol ethoxylate, alkylpolyglycoside, alkyldimethylamine oxide, ethoxylated fatty acid monoethanolamide, fatty acid monoethanolamide, or polyhydroxy alkyl fatty acid amide (e.g. as described in WO 92/06154).

The detergent composition may additionally comprise one or more other enzymes, such as e.g. proteases, amylases, lipases, cutinases, cellulases, peroxidases, oxidases, and further anti-microbial polypeptides.

The detergent may contain 1–65% of a detergent builder or complexing agent such as zeolite, diphosphate, triphosphate, phosphonate, citrate, nitrilotriacetic acid (NTA), ethylenediaminetetraacetic acid (EDTA), diethylenetriaminepentaacetic acid (DTA), alkyl- or alkenylsuccinic acid, soluble silicates or layered silicates (e.g. SKS-6 from Hoechst). The detergent may also be unbuilt, i.e. essentially free of detergent builder.

The detergent may comprise one or more polymers. Examples are carboxymethylcellulose (CMC), poly (vinylpyrrolidone) (PVP), polyethyleneglycol (PEG); poly (vinyl alcohol) (PVA), polycarboxylates such as polyacrylates, maleic/acrylic acid copolymers and lauryl methacrylate/acrylic acid copolymers.

The detergent may contain a bleaching system which may comprise a $H_2O_2$ source such as perborate or percarbonate which may be combined with a peracid-forming bleach activator such as tetraacetylethylenediamine (TAED) or nonanoyloxybenzenesulfonate (NOBS). Alternatively, the bleaching system may comprise peroxyacids of, e.g., the amide, imide, or sulfone type.

The detergent composition of the invention comprising the polypeptide of the invention may be stabilized using conventional stabilizing agents, e.g. a polyol such as propylene glycol or glycerol, a sugar or sugar alcohol, lactic acid, boric acid, or a boric acid derivative such as, e.g., an aromatic borate ester, and the composition may be formulated as described in, e.g., WO 92/19709 and WO 92/19708.

The detergent may also contain other conventional detergent ingredients such as, e.g., fabric conditioners including clays, foam boosters, suds suppressors, anti-corrosion agents, soil-suspending agents, anti-soil-redeposition agents, dyes, bactericides, optical brighteners, or perfume.

The pH (measured in aqueous solution at use concentration) will usually be neutral or alkaline, e.g. in the range of 7–11.

Particular forms of detergent compositions within the scope of the invention include:

1) A detergent composition formulated as a granulate having a bulk density of at least 600 g/l comprising

| | |
|---|---|
| linear alkylbenzenesulfonate (calculated as acid) | 7–12% |
| alcohol ethoxysulfate (e.g. $C_{12-18}$ alcohol, 1-2 EO) or alkyl sulfate (e.g. $C_{16-18}$) | 1–4% |
| alcohol ethoxylate (e.g. $C_{14-15}$ alcohol, 7 EO) | 5–9% |
| sodium carbonate (as $Na_2CO_3$) | 14–20% |
| soluble silicate (as $Na_2O, 2SiO_2$) | 2–6% |
| zeolite (as $NaAlSiO_4$) | 15–22% |
| sodium sulfate (as $Na_2SO_4$) | 0–6% |
| sodium citrate/citric acid (as $C_6H_5Na_3O_7/C_6H_8O_7$) | 0–15% |
| sodium perborate (as $NaBO_3.H_2O$) | 11–18% |
| TAED | 2–6% |
| carboxymethylcellulose | 0–2% |
| polymers (e.g. maleic/acrylic acid copolymer, PVP, PEG) | 0–3% |
| enzymes | 0–5% |
| minor ingredients (e.g. suds suppressors, perfume, optical brightener, photobleach) | 0–5% |

2) A detergent composition formulated as a granulate having a 40 bulk density of at least 600 g/l comprising

| | |
|---|---|
| linear alkylbenzenesulfonate (calculated as acid) | 6–11% |
| alcohol ethoxysulfate (e.g. $C_{12-18}$ alcohol, 1-2 EO) or alkyl sulfate (e.g. $C_{16-18}$) | 1–3% |
| alcohol ethoxylate (e.g. $C_{14-15}$ alcohol, 7 EO) | 5–9% |
| sodium carbonate (as $Na_2CO_3$) | 15–21% |
| soluble silicate (as $Na_2O, 2SiO_2$) | 1–4% |
| zeolite (as $NaAlSiO_4$) | 24–34% |
| sodium sulfate (as $Na_2SO_4$) | 4–10% |
| sodium citrate/citric acid (as $C_6H_5Na_3O_7/C_6H_8O_7$) | 0–15% |
| carboxymethylcellulose | 0–2% |
| polymers (e.g. maleic/acrylic acid copolymer, PVP, PEG) | 1–6% |
| enzymes | 0–5% |
| minor ingredients (e.g. suds suppressors, perfume) | 0–5% |

3) A detergent composition formulated as a granulate having a bulk density of at least 600 g/l comprising

| | |
|---|---|
| linear alkylbenzenesulfonate (calculated as acid) | 5–9% |
| alcohol ethoxylate (e.g. $C_{12-15}$ alcohol, 7 EO) | 7–14% |
| soap as fatty acid (e.g. $C_{16-22}$ fatty acid) | 1–3% |
| sodium carbonate (as $Na_2CO_3$) | 10–17% |
| soluble silicate (as $Na_2O, 2SiO_2$) | 3–9% |
| zeolite (as $NaAlSiO_4$) | 23–33% |
| sodium sulfate (as $Na_2SO_4$) | 0–4% |
| sodium perborate (as $NaBO_3.H_2O$) | 8–16% |
| TAED | 2–8% |
| phosphonate (e.g. EDTMPA) | 0–1% |
| carboxymethylcellulose | 0–2% |
| polymers (e.g. maleic/acrylic acid copolymer, PVP, PEG) | 0–3% |
| enzymes | 0–5% |
| minor ingredients (e.g. suds suppressors, perfume, optical brightener) | 0–5% |

4) A detergent composition formulated as a granulate having a bulk density of at least 600 g/l comprising

| | |
|---|---|
| linear alkylbenzenesulfonate (calculated as acid) | 8–12% |
| alcohol ethoxylate (e.g. $C_{12-15}$ alcohol, 7 EO) | 10–25% |
| sodium carbonate (as $Na_2CO_3$) | 14–22% |
| soluble silicate (as $Na_2O, 2SiO_2$) | 1–5% |
| zeolite (as $NaAlSiO_4$) | 25–35% |
| sodium sulfate (as $Na_2SO_4$) | 0–10% |
| carboxymethylcellulose | 0–2% |
| polymers (e.g. maleic/acrylic acid copolymer, PVP, PEG) | 1–3% |
| enzymes | 0–5% |
| minor ingredients (e.g. suds suppressors, perfume) | 0–5% |

5) An aqueous liquid detergent composition comprising

| | |
|---|---|
| linear alkylbenzenesulfonate (calculated as acid) | 15–21% |
| alcohol ethoxylate (e.g. $C_{12-15}$ alcohol, 7 EO or $C_{12-15}$ alcohol, 5 EO) | 12–18% |
| soap as fatty acid (e.g. oleic acid) | 3–13% |
| alkenylsuccinic acid ($C_{12-14}$) | 0–13% |
| aminoethanol | 8–18% |
| citric acid | 2–8% |
| phosphonate | 0–3% |
| polymers (e.g. PVP, PEG) | 0–3% |
| borate (as $B_4O_7$) | 0–2% |
| ethanol | 0–3% |
| propylene glycol | 8–14% |
| enzymes | 0–5% |
| minor ingredients (e.g. dispersants, suds suppressors, perfume, optical brightener) | 0–5% |

6) An aqueous structured liquid detergent composition comprising

| | |
|---|---|
| linear alkylbenzenesulfonate (calculated as acid) | 15–21% |
| alcohol ethoxylate (e.g. $C_{12-15}$ alcohol, 7 EO, or $C_{12-15}$ alcohol, 5 EO) | 3–9% |

-continued

| | |
|---|---|
| soap as fatty acid (e.g. oleic acid) | 3–10% |
| zeolite (as NaAlSiO$_4$) | 14–22% |
| potassium citrate | 9–18% |
| borate (as B$_4$O$_7$) | 0–2% |
| carboxymethylcellulose | 0–2% |
| polymers (e.g PEG, PVP) | 0–3% |
| anchoring polymers such as, e.g., lauryl methacrylate/acrylic acid copolymer; molar ratio 25:1; MW 3800 | 0–3% |
| glycerol | 0–5% |
| enzymes | 0–5% |
| minor ingredients (e.g. dispersants, suds suppressors, perfume, optical brighteners) | 0–5% |

7) A detergent composition formulated as a granulate having a bulk density of at least 600 g/l comprising

| | |
|---|---|
| fatty alcohol sulfate | 5–10% |
| ethoxylated fatty acid monoethanolamide | 3–9% |
| soap as fatty acid | 0–3% |
| sodium carbonate (as Na$_2$CO$_3$) | 5–10% |
| soluble silicate (as Na$_2$O, 2SiO$_2$) | 1–4% |
| zeolite (as NaAlSiO$_4$) | 20–40% |
| sodium sulfate (as Na$_2$SO$_4$) | 2–8% |
| sodium perborate (as NaBO$_3$.H$_2$O) | 12–18% |
| TAED | 2–7% |
| polymers (e.g. maleic/acrylic acid copolymer, PEG) | 1–5% |
| enzymes | 0–5% |
| minor ingredients (e.g. optical brightener, suds suppressors, perfume) | 0–5% |

8) A detergent composition formulated as a granulate comprising

| | |
|---|---|
| linear alkylbenzenesulfonate (calculated as acid) | 8–14% |
| ethoxylated fatty acid monoethanolamide | 5–11% |
| soap as fatty acid | 0–3% |
| sodium carbonate (as Na$_2$CO$_3$) | 4–10% |
| soluble silicate (as Na$_2$O, 2SiO$_2$) | 1–4% |
| zeolite (as NaAlSiO$_4$) | 30–50% |
| sodium sulfate (as Na$_2$SO$_4$) | 3–11% |
| sodium citrate (as C$_6$H$_5$Na$_3$O$_7$) | 5–12% |
| polymers (e.g. PVP, maleic/acrylic acid copolymer, PEG) | 1–5% |
| enzymes | 0–5% |
| minor ingredients (e.g. suds suppressors, perfume) | 0–5% |

9) A detergent composition formulated as a granulate comprising

| | |
|---|---|
| linear alkylbenzenesulfonate (calculated as acid) | 6–12% |
| nonionic surfactant, | 1–4% |
| soap as fatty acid | 2–6% |
| sodium carbonate (as Na$_2$CO$_3$) | 14–22% |
| zeolite (as NaAlSiO$_4$) | 18–32% |
| sodium sulfate (as Na$_2$SO$_4$) | 5–20% |
| sodium citrate (as C$_6$H$_5$Na$_3$O$_7$) | 3–8% |
| sodium perborate (as NaBO$_3$.H$_2$O) | 4–9% |
| bleach activator (e.g. NOBS or TAED) | 1–5% |
| carboxymethylcellulose | 0–2% |
| polymers (e.g. polycarboxylate or PEG) | 1–5% |
| enzymes | 0–5% |

-continued

| | |
|---|---|
| minor ingredients (e.g. optical brightener, perfume) | 0–5% |

10) An aqueous liquid detergent composition comprising

| | |
|---|---|
| linear alkylbenzenesulfonate (calculated as acid) | 15–23% |
| alcohol ethoxysulfate (e.g. C$_{12-15}$ alcohol, 2-3 EO) | 8–15% |
| alcohol ethoxylate (e.g. C$_{12-15}$ alcohol, 7 EO, or C$_{12-15}$ alcohol, 5 EO) | 3–9% |
| soap as fatty acid (e.g. lauric acid) | 0–3% |
| aminoethanol | 1–5% |
| sodium citrate | 5–10% |
| hydrotrope (e.g. Sodium toluenesulfonate) | 2–6% |
| borate (as B$_4$O$_7$) | 0–2% |
| carboxymethylcellulose | 0–1% |
| ethanol | 1–3% |
| propylene glycol | 2–5% |
| enzymes | 0–5% |
| minor ingredients (e.g. polymers, dispersants, perfume, optical brighteners) | 0–5% |

11) An aqueous liquid detergent composition comprising

| | |
|---|---|
| linear alkylbenzenesulfonate (calculated as acid) | 20–32% |
| alcohol ethoxylate (e.g. C$_{12-15}$ alcohol, 7 EO, or C$_{12-15}$ alcohol, 5 EO) | 6–12% |
| aminoethanol | 2–6% |
| citric acid | 8–14% |
| borate (as B$_4$O$_7$) | 1–3% |
| polymer (e.g. maleic/acrylic acid copolymer, anchoring polymer such as, e.g., lauryl methacrylate/acrylic acid copolymer) | 0–3% |
| glycerol | 3–8% |
| enzymes | 0–5% |
| minor ingredients (e.g. hydrotropes, dispersants, perfume, optical brighteners) | 0–5% |

12) A detergent composition formulated as a granulate having a bulk density of at least 600 g/l comprising

| | |
|---|---|
| anionic surfactant (linear alkylbenzenesulfonate, alkyl sulfate alpha-olefinsulfonate, alpha-sulfo fatty acid methyl esters, alkanesulfonates, soap) | 25–40% |
| nonionic surfactant (e.g. alcohol ethoxylate) | 1–10% |
| sodium carbonate (as Na$_2$CO$_3$) | 8–25% |
| soluble silicates (as Na$_2$O, 2SiO$_2$) | 5–15% |
| sodium sulfate (as Na$_2$SO$_4$) | 0–5% |
| zeolite (as NaAlSiO$_4$) | 15–28% |
| sodium perborate (as NaBO$_3$.4H$_2$O) | 0–20% |
| bleach activator (TAED or NOBS) | 0–5% |
| enzymes | 0–5% |
| minor ingredients (e.g. perfume, optical brighteners) | 0–3% |

13) Detergent formulations as described in 1)–12) wherein all or part of the linear alkylbenzenesulfonate is replaced by (C$^{12}$–C$_{18}$) alkyl sulfate.

14) A detergent composition formulated as a granulate having a bulk density of at least 600 g/l comprising

| ($C_{12}$–$C_{18}$) alkyl sulfate | 9–15% |
| --- | --- |
| alcohol ethoxylate | 3–6% |
| polyhydroxy alkyl fatty acid amide | 1–5% |
| zeolite (as $NaAlSiO_4$) | 10–20% |
| layered disilicate (e.g. SK56 from Hoechst) | 10–20% |
| sodium carbonate (as $Na_2CO_3$) | 3–12% |
| soluble silicate (as $Na_2O, 2SiO_2$) | 0–6% |
| sodium citrate | 4–8% |
| sodium percarbonate | 13–22% |
| TAED | 3–8% |
| polymers (e.g. polycarboxylates and PVP) | 0–5% |
| enzymes | 0–5% |
| minor ingredients (e.g. optical brightener, photo bleach, perfume, suds suppressors) | 0–5% |

15) A detergent composition formulated as a granulate having a bulk density of at least 600 g/l comprising

| ($C_{12}$–$C_{18}$) alkyl sulfate | 4–8% |
| --- | --- |
| alcohol ethoxylate | 11–15% |
| soap | 1–4% |
| zeolite MAP or zeolite A | 35–45% |
| sodium carbonate (as $Na_2CO_3$) | 2–8% |
| soluble silicate (as $Na_2O, 2SiO_2$) | 0–4% |
| sodium percarbonate | 13–22% |
| TAED | 1–8% |
| carboxymethyl cellulose | 0–3% |
| polymers (e.g. polycarboxylates and PVP) | 0–3% |
| enzymes | 0–5% |
| minor ingredients (e.g. optical brightener, phosphonate, perfume) | 0–3% |

16) Detergent formulations as described in 1)–15) which contain a stabilized or encapsulated peracid, either as an additional component or as a substitute for already specified bleach systems.

17) Detergent compositions as described in 1), 3), 7), 9) and 12) wherein perborate is replaced by percarbonate.

18) Detergent compositions as described in 1), 3), 7), 9), 12), 14) and 15) which additionally contain a manganese catalyst. The manganese catalyst may, e.g., be one of the compounds bleaching", Nature, 369, p. 637–639, 1994.

19) Detergent composition formulated as a nonaqueous detergent liquid comprising a liquid nonionic surfactant such as, e.g., linear alkoxylated primary alcohol, a builder system (e.g. phosphate), enzyme and alkali. The detergent may also comprise anionic surfactant and/or a bleach system.

The enzyme of the invention may be incorporated in concentrations conventionally employed in detergents. It is at present contemplated that, in the detergent composition of the invention, the enzyme in question with reduced allergenicity may be added in an amount corresponding to 0.001–100 mg of enzyme per liter of wash liquor.

Dishwashing Composition

Further, a modified enzyme according to the invention may also be used in dishwashing detergents.

Dishwashing detergent compositions comprise a surfactant which may be anionic, non-ionic, cationic, amphoteric or a mixture of these types. The detergent will contains 0–90% of non-ionic surfactant such as low- to non-foaming ethoxylated propoxylated straight-chain alcohols.

The detergent composition may contain detergent builder salts of inorganic and/or organic types. The detergent builders may be subdivided into phosphorus-containing and non-phosphorus-containing types. The detergent composition usually contains 1–90% of detergent builders.

Examples of phosphorus-containing inorganic alkaline detergent builders, when present, include the water-soluble salts especially alkali metal pyrophosphates, orthophosphates, and polyphosphates. An example of phosphorus-containing organic alkaline detergent builder, when present, includes the water-soluble salts of phosphonates. Examples of non-phosphorus-containing inorganic builders, when present, include water-soluble alkali metal carbonates, borates and silicates as well as the various types of water-insoluble crystalline or amorphous alumino silicates of which zeolites are the best-known, representatives.

Examples of suitable organic builders include the alkali metal, ammonium and substituted ammonium, citrates, succinates, malonates, fatty acid sulphonates, carboxymetoxy succinates, ammonium polyacetates, carboxylates, polycarboxylates, amino-polycarboxylates, polyacetyl carboxylates and polyhydroxsulphonates.

Other suitable organic builders include the higher molecular weight polymers and co-polymers known to have builder properties, for example appropriate polyacrylic acid, polymaleic and polyacrylic/polymaleic acid copolymers and their salts.

The dishwashing detergent composition may contain bleaching agents of the chlorine/bromine-type or the oxygen-type. Examples of inorganic chlorine/bromine-type bleaches are lithium, sodium or calcium hypochlorite and hypobromrite as well as chlorinated trisodium phosphate. Examples of organic chlorine/bromine-type bleaches are heterocyclic N-bromo and N-chloro imides such as trichloroisocyanuric, tribromoisocyanuric, dibromoisocyanuric and dichloroisocyanuric acids, and salts thereof with water-solubilizing cations such as potassium and sodium. Hydantoin compounds are also suitable.

The oxygen bleaches are preferred, for example in the form of an inorganic persalt, preferably with a bleach precursor or as a peroxy acid compound. Typical examples of suitable peroxy bleach compounds are alkali metal perborates, both tetrahydrates and monohydrates, alkali metal percarbonates, persilicates and perphosphates. Preferred activator materials are TAED and glycerol triacetate.

The dishwashing detergent composition of the invention may be stabilized using conventional stabilizing agents for the enzyme(s), e.g. a polyol such as e.g. propylene glycol, a sugar or a sugar alcohol, lactic acid, boric acid, or a boric acid derivative, e.g. an aromatic borate ester.

The dishwashing detergent composition of the invention may also contain other conventional detergent ingredients, e.g. deflocculant material, filler material, foam depressors, anti-corrosion agents, soil-suspending agents, sequestering agents, anti-soil redeposition agents, dehydrating agents, dyes, bactericides, fluorescers, thickeners and perfumes.

Finally, the enzyme of the invention may be used in conventional dishwashing detergents, e.g. in any of the detergents described in any of the following patent publications:

EP 518719, EP 518720, EP 518721, EP 516553, EP 516554, EP 516555, GB 2200132, DE 3741617, DE 3727911, DE 4212166, DE 4137470, DE 3833047, WO 93/17089, DE 4205071, WO 52/09680, WO 93/18129, WO 93/04153, WO 92/06157, WO 92/08777, EP 429124, WO 93/21299, U.S. Pat. No. 5141664, EP 561452, EP 561446, GB 2234980, WO 93/03129, EP 481547, EP 530870, EP 533239, EP 554943, EP 346137, U.S. Pat. No. 5112518,

EP-318204, EP 318279, EP 271155, EP 271156, EP 346136, GB 2228945, CA 2006687, WO 93/25651, EP 530635, EP 414197, U.S. Pat. No. 5240632.

Particular forms of dishwashing detergent compositions within the scope of the invention include:

1) POWDER AUTOMATIC DISHWASHING COMPOSITION

| | |
|---|---|
| Nonionic surfactant | 0.4–2.5% |
| Sodium metasilicate | 0–20% |
| Sodium disilicate | 3–20% |
| Sodium triphosphate | 20–40% |
| Sodium carbonate | 0–20% |
| Sodium perborate | 2–9% |
| Tetraacetylethylenediamine (TAED) | 1–4% |
| Sodium sulphate | 5–33% |
| Enzymes including modified enzymes | 0.0001–0.5% |

2) POWDER AUTOMATIC DISHWASHING COMPOSITION

| | |
|---|---|
| Nonionic surfactant (e.g. alcohol ethoxylate) | 1–2% |
| Sodium disilicate | 2–30% |
| Sodium carbonate | 10–50% |
| Sodium phosphonate | 0–5% |
| Trisodium citrate dihydrate | 9–30% |
| Nitrilotrisodium acetate (NTA) | 0–20% |
| Sodium perborate monohydrate | 5–10% |
| Tetraacetylethylenediamine (TAED) | 1–2% |
| Polyacrylate polymer (e.g. maleic acid/acrylic acid co-polymer) | 6–25% |
| Enzymes including modified enzymes | 0.0001–0.5% |
| Perfume | 0.1–0.5% |
| Water | 5–10 |

3) POWDER AUTOMATIC DISHWASHING COMPOSITION

| | |
|---|---|
| Nonionic surfactant | 0.5–2.0% |
| Sodium disilicate | 25–40% |
| Sodium citrate | 30–55% |
| Sodium carbonate | 0–29% |
| Sodium bicarbonate | 0–20% |
| Sodium perborate monohydrate | 0–15% |
| Tetraacetylethylenediamine (TAED) | 0–6% |
| Maleic acid/acrylic acid copolymer | 0–5% |
| Clay | 1–3% |
| Poly(amino acids) | 0–20% |
| Sodium polyacrylate | 0–8% |
| Enzymes including modified enzymes | 0.0001–0.5% |

4) POWDER AUTOMATIC DISHWASHING COMPOSITION

| | |
|---|---|
| Nonionic surfactant | 1–2% |
| Zeolite MAP | 15–42% |
| Sodium disilicate | 30–34% |
| Sodium citrate | 0–12% |
| Sodium carbonate | 0–20% |
| Sodium perborate monohydrate | 7–15% |
| Tetraacetylethylenediamine (TAED) | 0–3% |
| Polymer | 0–4% |
| Maleic acid/acrylic acid copolymer | 0–5% |
| Organic phosphonate | 0–4% |
| Clay | 1–2% |

4) POWDER AUTOMATIC DISHWASHING COMPOSITION —continued

| | |
|---|---|
| Enzymes including modified enzymes | 0.0001–0.5% |
| Sodium sulphate | Balance |

5) POWDER AUTOMATIC DISHWASHING COMPOSITION

| | |
|---|---|
| Nonionic surfactant | 1–7% |
| Sodium disilicate | 18–30% |
| Trisodium citrate | 10–24% |
| Sodium carbonate | 12–20% |
| Monopersulphate (2 $KHSO_5 \cdot KHSO_4 \cdot K_2SO_4$) | 15–21% |
| Bleach stabilizer | 0.1–2% |
| Maleic acid/acrylic acid copolymer | 0–6% |
| Diethylenetriaminepentaacetate, pentasodium salt | 0–2.5% |
| Enzymes including modified enzymes | 0.0001–0.5% |
| Sodium sulphate, water | Balance |

6) POWDER AND LIQUID DISHWASHING COMPOSITION WITH CLEANING SURFACTANT SYSTEM

| | |
|---|---|
| Nonionic surfactant | 0–1.5% |
| Octadecyl dimethylamine N-oxide dihydrate | 0–5% |
| 80:20 wt.C18/C16 blend of octadecyl dimethylamine N-oxide dihydrate and hexadecyldimethyl amine N-oxide dihydrate | 0–4% |
| 70:30 wt.C18/C16 blend of octadecyl bis (hydroxyethyl)amine N-oxide anhydrous and hexadecyl bis (hydroxyethyl)amine N-oxide anhydrous | 0–5% |
| $C_{13}$–$C_{15}$ alkyl ethoxysulfate with an average degree of ethoxylation of 3 | 0–10% |
| $C_{12}$–$C_{15}$ alkyl ethoxysulfate with an average degree of ethoxylation of 3 | 0–5% |
| $C_{13}$–$C_{15}$ ethoxylated alcohol with an average degree of ethoxylation of 12 | 0–5% |
| A blend of $C_{12}$–$C_{15}$ ethoxylated alcohols with an average degree of ethoxylation of 9 | 0–6.5% |
| A blend of $C_{13}$–$C_{15}$ ethoxylated alcohols with an average degree of ethoxylation of 30 | 0–4% |
| Sodium disilicate | 0–33% |
| Sodium tripolyphosphate | 0–46% |
| Sodium citrate | 0–28% |
| Citric acid | 0–29% |
| Sodium carbonate | 0–20% |
| Sodium perborate monohydrate | 0–11.5% |
| Tetraacetylethylenediamine (TAED) | 0–4% |
| Maleic acid/acrylic acid copolymer | 0–7.5% |
| Sodium sulphate | 0–12.5% |
| Enzymes including modified enzymes | 0.0001–0.5% |

7) NON-AQUEOUS LIQUID AUTOMATIC DISHWASHING COMPOSITION

| | |
|---|---|
| Liquid nonionic surfactant (e.g. alcohol ethoxylates) | 2.0–10.0% |
| Alkali metal silicate | 3.0–15.0% |
| Alkali metal phosphate | 20.0–40.0% |
| Liquid carrier selected from higher | 25.0–45.0% |

7) NON-AQUEOUS LIQUID AUTOMATIC DISHWASHING COMPOSITION

| | |
|---|---|
| glycols, polyglycols, polyoxides, glycolethers | |
| Stabilizer (e.g. a partial ester of phosphoric acid and a $C_{16}$–$C_{18}$ alkanol) | 0.5–7.0% |
| Foam suppressor (e.g. silicone) | 0–1.5% |
| Enzymes including modified enzymes | 0.0001–0.5% |

8) NON-AQUEOUS LIQUID DISHWASHING COMPOSITION

| | |
|---|---|
| Liquid nonionic surfactant (e.g. alcohol ethoxylates) | 2.0–10.0% |
| Sodium silicate | 3.0–15.0% |
| Alkali metal carbonate | 7.0–20.0% |
| Sodium citrate | 0.0–1.5% |
| Stabilizing system (e.g. mixtures of finely divided silicone and low molecular weight dialkyl polyglycol ethers) | 0.5–7.0% |
| Low molecule weight polyacrylate poylymer | 5.0–15.0% |
| Clay gel thickener (e.g. bentonite) | 0.0–10.0% |
| Hydroxypropyl cellulose polymer | 0.0–0.6% |
| Enzymes including modified enzymes | 0.0001–0.5% |
| Liquid carrier selected from higher lycols, polyglycols, polyoxides and glycol ethers | Balance |

9) THIXOTROPIC LIQUID AUTOMATIC DISHWASHING COMPOSITION

| | |
|---|---|
| $C_{12}$–$C_{14}$ fatty acid | 0–0.5% |
| Block co-polymer surfactant | 1.5–15.0% |
| Sodium citrate | 0–12% |
| Sodium tripolyphosphate | 0–15% |
| Sodium carbonate | 0–8% |
| Aluminum tristearate | 0–0.1% |
| Sodium cumene sulphonate | 0–1.7% |
| Polyacrylate thickener | 1.32–2.5% |
| Sodium polyacrylate | 2.4–6.0% |
| Boric acid | 0–4.0% |
| Sodium formate | 0–0.45% |
| Calcium formate | 0–0.2% |
| Sodium n-decydiphenyl oxide disulphonate | 0–4.0% |
| Monoethanol amine (MEA) | 0–1.86% |
| Sodium hydroxide (50%) | 1.9–9.3% |
| 1,2-Propanediol | 0–9.4% |
| Enzymes including modified enzymes | 0.0001–0.5% |
| Suds suppressor, dye, perfumes, water | Balance |

10) LIQUID AUTOMATIC DISHWASHING COMPOSITION

| | |
|---|---|
| Alcohol ethoxylate | 0–20% |
| Fatty acid ester sulphonate | 0–30% |
| Sodium dodecyl sulphate | 0–20% |
| Alkyl polyglycoside | 0–21% |
| Oleic acid | 0–10% |
| Sodium disilicate monohydrate | 18–33% |
| Sodium citrate dihydrate | 18–33% |
| Sodium stearate | 0–2.5% |
| Sodium perborate monohydrate | 0–13% |
| Tetraacetylethylenediamine (TAED) | 0–8% |
| Maleic acid/acrylic acid copolymer | 4–8% |
| Enzymes including modified enzymes | 0.0001–0.5% |

11) LIQUID AUTOMATIC DISHWASHING COMPOSITION CONTAINING PROTECTED BLEACH PARTICLES

| | |
|---|---|
| Sodium silicate | 5–10% |
| Tetrapotassium pyrophosphate | 15–25% |
| Sodium triphosphate | 0–2% |
| Potassium carbonate | 4–8% |
| Protected bleach particles, e.g. chlorine | 5–10% |
| Polymeric thickener | 0.7–1.5% |
| Potassium hydroxide | 0–2% |
| Enzymes including modified enzymes | 0.0001–0.5% |
| Water | Balance |

11) Automatic dishwashing compositions as described in 1), 2), 3), 4), 6) and 10), wherein perborate is replaced by percarbonate.

12) Automatic dishwashing compositions as described in 1)–6) which additionally contain a manganese catalyst. The manganese catalyst may, e.g., be one of the compounds described in "Efficient manganese catalysts for low-temperature bleaching", Nature, 369, (1994), p. 637–639.

Examples of readily available products containing protease for detergents include Alcalase®, Esperase®, Savinase® and Durazym® (all available from Novo Nordisk A/S); lipases for detergents include Lipolase® and Lipolase™ Ultra (available from Novo Nordisk A/S); cellulases for detergents such as Celluzyme®; α-amylases for detergents such as Termamyl®.

Personal Care Applcications

The conjugated polypeptide of the invention is also of interest in connection with personal care applications.

Proteases

Proteases are well-known active ingredients for cleaning of contact lenses. They hydrolyse the proteinaceous soil on the lens and thereby makes it soluble. Removal of the protein soil is essential for the wearing comfort.

Proteases are also effective ingredients in skin cleaning products, where they remove the upper layer of dead keratinaseous skin cells and thereby makes the skin look brighter and more fresh.

Proteases are also used in oral care products, especially for cleaning of dentures, but also in dentifrices.

Further, proteases are used in toiletries, bath and shower products, including shampoos, conditioners, lotions, creams, soap bars, toilet soaps, and liquid soaps.

Lipases

Lipases can be applied for cosmetic use as active ingredients in skin cleaning products and anti-acne products for removal of excessive skin lipids, and in bath and shower products such as creams and lotions as active ingredients for skin care.

Lipases can also be used in hair cleaning products (e.g. shampoos) for effective removal of sebum and other fatty material from the surface of hair.

Lipases are also effective ingredients in products for cleaning of contact lenses, where they remove lipid deposits from the lens surface.

Oxidoreductases

The most common oxidoreductase for personal care purposes is an oxidase (usually glucose oxidase) with substrate (e.g. glucose) that ensures production of $H_2O_2$, which then will initiate the oxidation of for instance SCN or $I^-$ into antimicrobial reagents ($SCNO^-$ or $I_2$) by a peroxidase (usually lactoperoxidase). This enzymatic complex is known in nature from e.g. milk and saliva.

It is being utilised commercially as anti-microbial system in oral care products (mouth rinse, dentifrice, chewing gum) where it also can be combined with an amyloglucosidase to produce the glucose. These systems are also known in cosmetic products for preservation.

Anti-microbial systems comprising the combination of an oxidase and a peroxidase are know in the cleaning of contact lenses.

Another application of oxidoreductases are oxidative hair dyeing using oxidases, peroxidases and laccases.

Free radicals formed an the surface of the skin (and hair) known to be associated with the ageing process of the skin (spoilage of the hair).

The free radicals activate chain reactions that leads to destruction of fatty membranes, collagen, and cells. The application of free radical scavengers such as Superoxide dismutase into cosmetics is well-known (R. L. Goldemberg, DCI, Nov. 93, p. 48–52).

Protein disulfide isomerase (PDI) is also an oxidoreductase. It can be utilised for waving of hair (reduction and reoxidation of disulfide bonds in hair) and repair of spoiled hair (where the damage is mainly reduction of existing disulfide bonds), Carbohydrases Plaque formed on the surface of teeth is composed mainly of polysaccharides. They stick to the surface of the teeth and the microorganisms. The polysaccharides are mainly α-1,6 bound glucose (dextran) and α-1,3 bound glucose (mutan). The application of different types of glucanases such as mutanase and dextranase helps hydrolysing the sticky matrix of plaque, making it easier to remove by mechanical action.

Also other kinds of biofilm for instance the biofilm formed in lens cases can be removed by the action of glucanases.

Anti-microbial Polypeptides

Anti-microbial polypeptides have widespread applications such as for preservation of cosmetic products, anti-acne products, deodorants and shampoos. Further such polypeptides may be use in contact lens products.

Food and Feed

Further conjugated enzymes or polypeptides with reduced allergenicity according to the invention may advantageously be used in the manufacturing of food and feed.

Proteases

The gluten in wheat flour is the essential ingredient responsible for the ability of flour to be used in baked foodstuffs. Proteolytic enzymes are sometimes needed to modify the gluten phase of the dough, e.g. a hard wheat flour can be softened with a protease.

Neutrase® is a commercially available neutral metallo protease that can be used to ensure a uniform dough quality and bread texture, and to improve flavour. The gluten proteins is degraded either moderately or more extensively to peptides, whereby close control is necessary in order to avoid excessive softening of the dough.

Proteases are also used for modifying milk protein.

To coagulate casein in milk when producing cheese proteases such as rennet or chymosin may be used.

In the brewery industry proteases are used for brewing with unmalted cereals and for controlling the nitrogen content.

In animal feed products proteases are used so to speak to expand the animals digestion system.

Lipases

The application of lipase in the baking industry is rather new. Addition of lipase results in improved dough properties and an improved breadmaking quality in terms of larger volume, improved crumb structure and whiter crumb colour. The observed effect can be explained by a mechanism where the lipase changes the interaction between gluten and some lipids fragment during dough mixing. This results in an improved gluten network.

The flavour development of blue roan cheeses (e.g. Danablue), certain Italian cheese types and other dairy products containing butter fat are dependent on the degradation of milk fat into free fatty acids. Lipases may be used for developing flavour in such products.

In the oil- and fat producing industry lipases are used e.g. to minimize the amount of undesirable side-products, to modify fats by interesterification, and to synthesis of esters.

Oxidoreductases

Further oxidoreductases with reduced allergenicity according tc, the invention may advantageously be used in the manufacturing of food and feed.

Several oxidoreductases are used for baking, glucose oxidase, lipoxygenase, peroxidase, catalase and combinations hereof. Traditionally, bakers strengthen gluten by adding ascorbic acid and potassium bromate. Some oxidoreductases can be used to replace bromate in dough systems by oxidation of free sulfydryl units in gluten proteins. Hereby disulphide linkages are formed resulting in stronger, more elastic doughs with greater resistance.

Gluzyme™ (Novo Nordisk A/S) is a glucose oxidase preparation with catalase activity that can be used to replace bromate. The dough strengthen is measured as greater resistance to mechanical shock, better oven spring and larger loaf volume.

Carbohydrases

Flour has varying content of amylases leading to differences in the baking quality. Addition of amylases can be necessary in order to standardize the flour. Amylases and pentosanases generally provide sugar for the yeast fermentation, improve the bread volume, retard retrogradation, and decrease the staling rate and stickiness that results from pentosan gums. Examples of carbohydrases is given below.

Certain maltogenic amylases can be used for prolonging the shelf life of bread for two or more days without causing gumminess in the product. Selectively modifies the gelatinized starch by cleaving from the non-reducing end of the starch molecules, low molecular weight sugars and dextrins. The starch is modified in such a way that retrogradation is less likely to occur. The produced low-molecular-weight sugars improve the baked goods water retention capacity without creating the intermediate-length dextrins that result in gumminess in the finished product. The enzyme is inactivated during bread baking, so it can be considered a processing aid which does not have to be declared on the label overdosing of Novamyl can almost be excluded.

The bread volume can be improved by fungal α-amylases which further provide good and uniform structure of the bread crumb. Said α-amylases are endoenzymes that produce maltose, dextrins and glucose. Cereal and some bacterial α-amylases are inactivated at temperatures above the gelatinization temperature of starch, therefore when added to a wheat dough it results in a low bread volume and a sticky bread interior. Fungamyl has the advantage of being thermolabile and is inactivated just below the gelatinization temperature.

Enzyme preparations containing a number of pentosanase and hemi-cellulase activities can improve the handling and stability of the dough, and improves the freshness, the crumb structure and the volume of the bread.

By hydrolysing the pentosans fraction in flour, it will lose a great deal of its water-binding capacity, and the water will then be available for starch and gluten. The gluten becomes more pliable and extensible, and the starch gelatinize more easily. Pentosanases can be used in combination with or as an alternative to emulsifiers.

Further carbohydrases are user for producing syrups from starch, which are widely used in soft drinks, sweets, meat products, dairy products, bread products, ice cream, baby food, jam etc.

The conversion of starch is normally carried out three steps. First the starch is liquefied, by the use of α-amylases. Maltodextrins, primary consisting of oligosaccharides and dextrins, are obtained.

The mixture is then treated with an amyloglucosidase for hydrolysing the oligosaccharides and dextrins into glucose. This way a sweeter product is obtained. If high maltose syrups are desired β-amylases alone or in combination with a pullulanase de-branching enzyme) may be used.

The glucose mixture can be made even sweeter by isomerization to fructose. For this an immobilized glucose isomerase can be used.

In the sugar industry, it is common practice to speed up the break down of present starch in cane juices. Thereby the starch content in the raw sugar is reduced and filtration at the refinery facilitated.

Furthermore dextranases are used to break down dextran in raw sugar juices and syrups.

In the alcohol industry α-amylases, is advantageously being used for thinning of starch in distilling mashes.

In the brewing industry α-amylases is used for adjunct liquefaction.

In the dairy industry galactosidases (lactase) is used when producing low lactose milk for persons suffering from lactose malabsorption.

When flavoured milk drinks are produced from lactase-treated milk, the addition of sugar can be reduced without reducing the sweetness of the product.

In the production of condensed milk, lactose crystallization can be avoided by lactase treatment, and the risk of thickening caused by casein coagulation in lactose crystals is thus reduced.

When producing ice cream made from lactase-treated milk (or whey) no lactose crystals will be formed and the defect, sandiness, will not occur.

Further, xylanases are known to be used within a number of food/feed industrial applications as described in WO 94/21785 (Novo Nordisk A/S).

α-amylases are used in the animal feed industry to be added to cereal-containing feed to improve the digestibility of starch.

Anti-microbial Polypeptides

Certain bacteriolytic enzymes may be used e.g. to wash carcasses in the meat packing industry (see U.S. Pat. No. 5,354,681 from Novo Industri A/S)

Transferases

Transglutaminases with reduced allergenicity according to the invention may advantageously be used in the manufacturing of food and feed.

Transglutaminases has the ability to crosslinking protein.

This property can be used for gelling of aqueous phases containing proteins. This may be used for when producing of spreads (DK patent application no. 1071/84 from Novo Nordisk A/S).

Transglutaminases are being used for improvement of baking quality of flour e.g. by modifying wheat flour to be used in the preparation of cakes with improved properties, such as improved taste, dent, mouth-feel and a higher volume (see JP 1-110147).

Further producing paste type food material e.g. used as fat substitution in foods as ice cream, toppings, frozen desserts, mayonnaises and low fat spreads (see WO 93/22930 from Novo Nordisk A/S).

Furthermore for preparation of gels for yoghurt, mousses, cheese, puddings, orange juice, from milk and milk-like products, and binding of chopped meat product, improvement of taste and texture of food proteins (see WO 94/21120 and WO 94/21129 from Novo Nordisk A/S).

Phytases

Phytases of the invention may advantageously be used in the manufacturing of food, such as breakfast cereal, cake, sweets, drink, bread or soup etc., and animal feed.

Phytases may be used either for exploiting the phosphorus bound in the phytate/phytic acid present in vegetable protein sources or for exploiting the nutritionally important minerals bound in phytic acid complexes.

Microbial phytase may be added to feedstuff of monogastric animals in order to avoid supplementing the feed with inorganic phosphorus (see U.S. Pat. No. 3,297,548)

Further phytases may be used in soy processing. Soybean meal may contain high levels of the anti-nutritional factor phytate which renders this protein source unsuitable for application in baby food and feed for fish, calves and other non-ruminants, since the phytate chelates essential minerals present therein (see EP 0 420 358).

Also for baking purposes phytases may be used. Bread with better quality can be prepared by baking divided pieces of a dough containing wheat flour etc. and phytase (see JP-0-3076529-A)

A high phytase activity koji mold are known to be used for producing refined sake (see JP-0-6070749-A).

Textile Applications

Proteases

Proteases are used for degumnming and sand-washing of silk.

Lipases

Lipases are used for removing fatty matter containing hydrophobic esters (e.g. triglycerides) during the finishing of textiles (see e.g. WO 93/13256 from Novo Nordisk A/S).

Oxidoreductases

In bleach clean-up of textiles catalases may serve to remove excess hydrogen peroxide.

Carbohydrases

Cellulolytic enzymes are widely used in the finishing of denim garments in order to provide a localized variation in the colour density of the fabric (Enzyme facilitated "stone wash").

Also cellulolytic enzymes find use in the bio-polishing process. Bio-Polishing is a specific treatment of the yarn surface which improves fabric quality with respect to handle and appearance without loss of fabric wettability. Bio-polishing may be obtained by applying the method described e.g. in WO 93/20278.

During the weaving of textiles, the threads are exposed to considerable mechanical strain. In order to prevent breaking, they are usually reinforced by coating (sizing) with a gelatinous substance (size). The most common sizing agent is starch in native or modified form. A uniform and durable finishing can thus be obtained only after removal of the size from the fabric, the so called desizing. Desizing of fabrics sized with a size containing starch or modified starch is preferably facilitated by use of amylolytic enzymes.

Oral and Dermal Pharmaceuticals

Proteases

Different combinations of highly purified proteases (e.g. Trypsin and Chymotrypsin) are used in pharmaceuticals to be taken orally, and dermal pharmaceuticals for combating e.g. inflammations, edemata and injuries.

Leather Production

Transferase

Transglutaminase is known to be used for casein finishing of leather by acting as a hardening agent (see WO 94/13839 from Novo Nordisk).

Hard Surface Cleaning

Cleaning of hard surfaces e.g. in the food industry is often difficult, as equipment used for producing dairies, meat, sea food products, beverages etc. often have a complicated shape. The use of surfactant compositions in the form gels and foams comprising enzymes have shown to facilitate and improve hard surface cleaning. Enzymes, which advantageously may be added in such surfactant compositions, are in particular proteases, lipases, amylases and cellulases.

Such hard surface cleaning compositions comprising enzymes may also advantageously be used in the transport sector, for instance for washing cars and for general vessel wash.

Finally the invention relates to the use of the conjugate of the invention or a composition of the invention in products comprising polypeptides.

First of all the conjugate or compositions of the invention can advantageously be used for personal care products, such as hair care and hair treatment products. This include products such as shampoo, balsam, hair conditioners, hair waving compositions, hair dyeing compositions, hair tonic, hair liquid, hair cream, shampoo, hair rinse, hair spray.

Further contemplated is oral care products such as dentifrice, mouth washes, chewing gum.

Also contemplated is skin care products and cosmetics, such as skin cream, skin milk, cleansing cream, cleansing lotion, cleansing milk, cold cream, cream soap, nourishing essence, skin lotion, milky lotion, calamine lotion, hand cream, powder soap, transparent soap, sun oil, sun screen, shaving foam, shaving cream, baby oil lipstick, lip cream, creamy foundation, face powder, powder eye-shadow, powder, foundation, make-up base, essence powder, whitening powder.

Also for contact lenses hygiene products the conjugate of the invention can be used advantageously. Such products include contact lenses cleaning and disinfection products.

The use for detergents such as washing powder, soap, soap bars, liquid soap are also contemplated.

METHODS AND MATERIALS

Materials:

Enzyme Substrate suc-AAPF-pNA (succinyl-Alanine-Alanine-Proline-Phenylalanine-para-nitroanilide. Sigma no. S-7388, $M_w$ 624.6 g/mole Dimethyl-casein (CM-casein) (Sigma)

Glycerol tributyrate (Merck 1958)

Cellazyme-C® (Megazyme)

Carboxy methyl cellulose (Sigma)

Polymers:

Polyethylene glycol (PEG-35.000) from Fluka

Polyethylene glycol (PEG-5.000) activated by Tresyl chloride (2,2,2-triflouroethansulfonyl chloride) (Sigma, St. Louis, USA; M-3038)

mono-methoxypolyethylene glycol (mPEG-5.000) from Shearwater Polymers Inc., USA.

mono-methoxypolyethylene glycol (mPEG-15.000) from Shearwater Polymers Inc., USA.

mPEG-NH$_2$-5000 (Shearwater Polymers Inc., USA)

Enzymes:

Esperase® (available from Novo Nordisk A/S)

Subtilisin A (Novo Nordisk A/S)

Subtilisin Novo (Subtilisin BNP') (Novo Nordisk A/S)

Lipolase®: *Humicola lanuginosa* lipase described in EP 305 216 (available from Novo Nordisk A/S)

Lipolase® variant A: Lipolase® with the following mutations E87K/D254K (available from Novo Nordisk A/S)

*Candida antarctica* lipase B (available on request from Novo Nordisk A/S).

*Polyporus pinsitus* laccase described in PCT/U.S. Pat. No. 95/07536 from Novo Nordisk Biotech Inc.

*Coprinus cinereus* peroxidase (available from Novo Nordisk A/S on request).

Carezyme® (Novo Nordisk A/S)

Solutions:

Stop-solution (DMG-buffer)

Sodium Borate, borax (Sigma)

3,3-Dimethyl glutaric acid (Sigma)

CaCl$_2$ (Sigma)

Tresyl chloride (2,2,2-triflouroethansulfonyl chloride) (Fluka) Tween 20: Poly oxyethylene sorbitan mono laurate (Merck cat no. 822184)

1-ethyl-3-(3-dimethylaminopropyl)carbodiimide (EDC) (Fluka) N-Hydroxy succinimide (Fluka art. 56480))

Phosgene (Fluka art. 79380)

Tracer molecule:

biotinylated Mouse anti Rat IgE (Zymed, no. 03-9740)

Colouring substrate:

OPD: o-phenylene-diamine, (Kementec cat no. 4260)

Animals:

Brown Norway rats (from Charles River, Del.)

Equipment:

XCEL II (Novex)

ELISA reader (UVmax, Molecular Devices)

HPLC (Waters)

PFLC (Pharmacia)

Superdex column, Mono-Q, Mono S from Pharmacia, SW.

Superdex-75 column (Pharmacia, SW)

SLT: Fotometer from SLT LabInstruments

Size-exclusion chromatograph (Spheragel TSK-G2000 SWG).

Size-exclusion chromatograph (Superdex 200, Pharmacia, SW)

Methods:

Protease activity using casein as substrate

The Esperase® activity determined using casein as the substrate is described in "AF 219/1-GB (available from Novo Nordisk A/S)

Protease activity analysis with Suc-Ala-Ala-Pro-Phe-nNA:

Proteases especially chymotrypsin cleaves the bond between the peptide and p-nitroaniline to give a visible yellow colour absorbing at 405 nm.

Buffer: e.g. Britton and Robinson buffer, pH 8.3

Substrate: 10 mg suc-AAPF-pNA is dissolved into 1 ml dimethyl sulfoxide (DMSO). 100 µl of this is diluted into 10 ml with Britton and Robinson buffer.

Analysis: Substrate and protease solution is mixed and the absorbance is monitored at 405 nm as a function of time and $ABS_{405\ nm}$/min. The temperature should be controlled (20–50° C. depending on protease). This is a measure of the protease activity in the sample.

Lipase Activity:

The lipase activity was analysed as described in "AF 95/5 GB (available from Novo Nordisk on request)

Oxidoreductase activity

The Oxidoreductase activity determined using casein as the substrate is described in "AF 21911-GB (available from Novo Nordisk A/S).

Laccase Activity

Laccase activity is determined from the oxidation of syringaldazin under aerobic conditions. The violet colour produced is photometered at 530 nm. The analytical conditions are 19 $\mu$M syringaldazin, 23.2 mM acetate buffer, pH 5.5, 30° C., 1 min. reaction time. 1 laccase unit (LACU) is the amount of enzyme that catalyses the conversion of 1.0 $\mu$mole syringaldazin per minute at these conditions.

The laccase activity of laccases is described in AF 239 GB which are hereby included as reference (available on request from Novo Nordisk).

Peroxidase Activity

The enzyme activity of the peroxidase is measured in PODU (peroxidase units). 1 PODU is the amount of enzymes that catalyses the conversion of 1 $\mu$mol $H_2O_2$ per minute in a system where 2,2'-azinobis[3-ethylbenzothiazoline-6-sulfonate], ABTS, is oxidized. A detailed description of Novo Nordisk's analytical method is available on request (AF 279/1 GB).

Cellulase Activity

The enzymatic activity of Carezymes was measured as release of blue dye from azurine-crosslinked HE-cellulose (Cellazyme-C®). The reaction was carried out at 40° C. in 20 mM Na-phosphate pH 7 for 10 minutes. Release of dye was monitored by reading the absorbance at 595 nm in a UVmax® Elisa-reader. In addition, cellulytic activity was measured as described in "EAL-SM-0373.01/01" (available from Novo Nordisk on request).

ELISA IgE Test System.

A three layer sandwich ELISA is used to determine relative concentrations of specific antibodies.

The immunizing molecule is used as coating antigen with 10 $\mu$g per ml and 50 $\mu$l per well, in neutral phosphate buffer, incubated overnight at 4° C. All remaining binding spots an the well surface are blocked in 2% skim milk, 200 $\mu$l per well in phosphate buffer for at least 30 minutes at room temperature (RT). All seras to be tested with this antigen are added at 50 $\mu$l per well to this plate using a 8-channel pipette in dilution series from 10×diluted followed by 3-fold dilutions. Dilutions are made i phosphate buffer with 0.5% skim milk and 0.05% Tween20, incubated 2 hours on agitation platform at RT. The "tracer" molecule is biotinylated Mouse anti Rat IgE 50 $\mu$l per well and diluted 2000×in phosphate buffer with 0.5% skim milk and 0.05% Tween 20, incubated 2 hours on an agitation platform at RT. Control (blank) was identical sequence but without rat sera. 50 $\mu$l per well streptavidin horse raddish peroxidase, diluted 2000×was incubated 1 hour on an agitation platform. Colouring substrate at 50 $\mu$l per well is OPD (6 mg) and $H_2O_2$ (4 $\mu$l of a 30% solution) per 10 ml citrate buffer pH 5.2. The reaction is stopped using 100 $\mu$l per well 2N $H_2SO_4$. All readings on SLT at 486 nm and 620 nm as reference. Data is calculated and presented in Lotus.

Intratracheal (IT) Stimulation of Rats

For IT administration of molecules disposable syringes with a 2½ long metal probe is used. This probe is instilled in the trachea (see FIG. 1) approximately 1 cm below the epiglotis (see FIG. 1), and 0.1 ml of a solution of the molecules is deposited. The animals are stimulated 4 times, with 5 days between the last stimulation and exsanguination.

Animals are Brown Norway rats, in groups of 4. Weight at time of start is more than 250 grams and at termination-approximatly 450 grams Determination of the Molecular Weight Electrophoretic separation of proteins was performed by standard methods using 4–20% gradient SDS poly acrylamide gels (Novex). Proteins were detected by silver staining. The molecular weight was measured relative to the mobility of Mark-12® wide range molecular weight standards from Novex.

EXAMPLES

Example 1

Activation of PEG 35.000 with Tresyl chloride

The activation method is adapted from Nilson, K. et al., (1984), supra. All solvents used are Merck analytical grade.

4.0 g PEG 35.000 was dissolved in anhydrous dichloromethane (10 ml). Pyridine (0.25 ml) and Tresyl chloride (0.22 ml) was added. Upon stirring for 90 minutes at ambient temperature the obtained yellow mixture was evaporated to dryness and dissolved in hot ethanol (60 ml) and made acidic with HCl. A voluminous white precipitate was obtained upon leaving the mixture overnight at −18° C. in a freezer. The precipitate was recovered by centrifugation at 400 g for 20 minutes and washed repeatedly (6 times) with cold acidic ethanol (60 ml ethanol, 0.5 ml concentrated HCl). The activated PEG-35.000 was recovered by evaporation of solvents until constant weight was obtained of an off-white powder in a yield of 77%. The activated PEG-35.000 was characterised by melting point 59–61° C. and NMR analysis indicated 30–35% tresylation.

In a scale up synthesis following the above method a yield of 96% with melting point 59–60° C. light yellow flakes was obtained. The NMR analysis showed above 40% tresylation.

Example 2

Activation of mPEG 15.000 with Tresyl chloride mPEG 15.000 (10.0 g) was dissolved in dichloromethane (anhydrous 35 ml) of which 15 ml was distilled off to remove any trace of water. After cooling triethylamine (900 $\mu$l, 10 eqv.) and Tresyl chloride (350 $\mu$l, 5 eqv.) was added below the surface. The solution turned light yellow and some triethylamine, hydrochloride precipitated. After 90 min the solution was poured into ether (250 ml) in a thin squirt and with stirring. After 3 min. of stirring the light yellow precipitate was filtered, washed with ether (20 ml) and dried to yield 11.3 g NMR showing 80–90% activation and significant amounts of $HNEt_3Cl$. This was recrystallised from ethyl acetate (325 ml) with warm filtration to remove most of the salt. After slow cooling to room temperature the suspension was left in the refrigerator for further crystallisation. Yielding 9.3 g (93%) of white crystals. $^1$H-NMR ($CDCl_3$) $\delta$ 1.42 t (I=6.5 $CH_3$ i $HNEt_3Cl$), 3.10 dq (I=4.6 C i $HNEt_3Cl$), 3.38 s (I=2.6 $CH_3$ i OMe), 3.40* dd (I=4.5%, $^{13}$C satellite), 3.64 bs (I=1364 main peak), 3.89* dd (I=4.8%, $^{13}$C satellite), 4.24 q (J=9.0 Hz, I=1.8, $CH_2$ in tresyl), 4.53* dd (I=1.5 $CH_2$-O-Tresyl) Indicating 80–90% activation and only 6% (w/w) $INEt_3Cl$.

Example 3

Activation of mPEG 15.000 with N-succinimidyl carbonate mPEG 15.000 was suspended in toluene (4 ml/g of mPEG) 20% was disilled off at normal pressure to dry the reactants azeotropically. Dichloromethane (dry 1 ml/g mPEG) was added when the solution was cooled to 30° C. and phosgene in toluene (1.93M-5 mole/mole mPEG) was added and mixture stirred at room temperature over night. The mixture was evaporated to dryness and the desired product was obtained as waxy lumps.

After evaporation dichloromethane and toluene (1:2, dry 3 ml/g mPEG) was added to redissolve the white solid. N-Hydroxy succinimide (2 mole/mole mPEG.) was added as a solid and then triethylamine (1.1 mole/mole mPEG). The mixture was stirred for 3 hours. initially unclear, then clear and ending with a small precipitate. The mixture was evaporated to dryness and recrystallised from ethyl acetate (10 ml) with warm filtration to remove salts and insoluble traces. The blank liquid was left for slow cooling at ambient temperature for 16 h and then in the refrigerator over night. The white precipitate was filtered and washed with a little cold ethyl acetate and dried to yield 98% (w/w). NMR Indicating 80–90% activation and 5% (w/w) $HNEt_3Cl$. $^1$H-NMR for mPEG 15000 ($CDCl_3$) δ 1.42 t (I=4.8 $CH_3$ i $HNEt_3Cl$), 2.84 s (I=3.7 succinimide), 3.10 dq (I=3.4 $CH_2$ i $HNEt_3Cl$), 3.38 s (I=2.7 $CH_3$ i OMe), 3.40* dd (I=4.5%, $^{13}$C satellite), 3.64 bs (I=1364 main peak), 3.89* dd (I=4.8%, ($^{13}$C satellite), 4.47 dd (I=1.8, $CH_2$ in PEG). No change was seen after storage in desiccator at 22° C. for 4 months.

Example 4

Activation of mPEG 5.000 with N-succinimidyl carbonate

Activation of mPEG 5.000 with N-succinimidyl carbonate was performed as described in Example 3.

Example 5

Conjugation of protease with Tresyl chloride-activated PEG-35.000

A mixture (7.5 ml) of 70 mg of highly purified Esperase® and 855 mg of activated PEG 35.000 prepared according to example 1 was incubated in 0.1M Na-Borate, pH 9.2, at ambient temperature overnight using magnetic stirring. The conjugation was terminated by addition of ethanol amine (0.01 ml).

The resulting Esperase® PEG 35.000 conjugate was purified by size-exclusion chromatography by HPLC using a Superdex-75 column.

Compared to the parent enzyme the conjugate held 68% residual enzyme activity in peptide assay using suc-AAPF-pNA as substrate and 39% residual enzyme activity the assay using casein as substrate.

Example 6

Using the same procedure and chemicals as describe in the above examples 1 and 6, with approximately 10 times surplus of activated PEG 35.000, e.g. 42 mg of Esperase® and 480 mg of activated PEG residual activities relative to the parent enzyme are 80% using the suc-AAPF-F-pNA-substrate and 46% with casein as substrate.

Example 7

Conjugation of protease with activated mPEG 5.000

200 mg of Subtilisin Novo was incubated in 50 mM NaBorate, pH 10, with 1.8 g of activated mPEG 5.000 with N-succinimidyl carbonate (prepared according to Example 4), in a final volume of 20 ml. The reaction was carried out at ambient temperature using magnetic stirring. Reaction time was 1 hour. The reaction was stopped by adding DMG buffer to a final concentration of 5 mM dimethyl glutarate, 1 mM $CaCl_2$ and 50 mM borate, pH 5.0.

The molecular weight of the obtained derivative was approximately 100 kDa, corresponding to 12 moles of PEG attached per mole Subtilisin Novo.

Compared to the parent enzyme, residual activity was close to 100% towards peptide substrate (succinyl-Ala-Ala-Pro-Phe-p-Nitroanilide) and 64% towards CM-casein.

Example 8

Conjugation of protease with activated mPEG 15.000

200 mg of Subtilisin Novo was incubated in 50 mM NaBorate pH 10 with 5.5 g of activated mPEG 15.000 N-succinimidyl carbonate (prepared according to Example 3), in a final volume of 20 ml. The reaction was carried out at ambient temperature using magnetic stirring. Reaction time was 1 hour. The reaction was stopped by adding DMG buffer to a final concentration of 5 mM dimethyl glutarate, 1 mM $CaCl_2$ and 50 mM borate, pH 5.0.

The molecular weight of the obtained derivative was above 200 kDa, corresponding to 12 moles of PEG attached per mole Subtilisin Novo.

Compared to the parent enzyme, residual activity was close to 100% towards peptide substrate (succinyl-Ala-Ala-Pro-Phe-p-Nitroanilide) and 71% towards CM-casein.

Example 9

Conjugation of lipase with Tresyl chloride activated PEG 35.000

A mixture (3.4 ml) of 40 mg of highly purified Lipolase® and 440 mg of activated PEG 35.000 prepared according to example 1 was incubated in 0.1M Na-Borate, pH 9.2, at ambient temperature over night using magnetic stirring. The conjugation was terminated by addition of ethanol amine (0.01 ml).

The resulting Lipolase®-PEG 35.000 conjugate was purified by size-exclusion chromatography by HPLC using a Superdex-75 column.

Compared to the parent lipase the conjugate held 56% residual enzyme activity using glycerol tributyrate as substrate.

Example 10

Conjugation of lipase with Tresyl chloride activated PEG 5.000

A mixture (2 ml) of 25 mg of highly purified Lipolase® and 363 mg of Tresyl chloride activated PEG 5.000 was incubated in 0.1M Na-Borate, pH 9.2, at ambient temperature over night using magnetic stirring. The conjugation was terminated by addition of ethanol amine (0.01 ml).

The resulting Lipolase®-PEG 5.000 conjugated was purified by size-exclusion chromatography by HPLC using a Superdex-75 column.

Compared to the parent enzyme the conjugate held 48% residual enzyme activity using glycerol tributyrate as substrate.

Example 11

Conjugation of lipase with Tresyl chloride activated mPEG 15.000

25 mg of *Candida antarctica* lipase B in 25 ml of 0.1M borate, 1M NaCl, pH 9.2, was incubated with 2.82 gram of mPEG 15.000 activated with Tresyl chloride according to Example 2 for 3 hours at ambient temperature. The reaction was stopped by addition of 1 ml 2M Glycine and the derivative purified by size-exclusion chromatography (Spherogel TSK-G2000 SWG).

Relative to the parent *Candida antarctica* lipase B the derivative retained some 83% residual enzyme activity using glycerol tributyrate as substrate.

Example 12

Conjugation of lipase with Tresyl chloride activated mPEG 15.000

27 mg of Lipolase® variant A in 6 ml of 0.1M borate, 0.8M NaCl, pH 9.2 was incubated with 417.4 mg of PEG 15.000 activated with Tresyl Chloride according to Example 2 for 3 hours at ambient temperature. The reaction was stopped by addition of 139 µl 2M Glycine and the derivative purified by size-exclusion chromatography (Spherogel TSK-G2000 SWG).

Relative to the parent Lipolase® variant the derivative retained some 36% residual enzyme activity using glycerol tributyrate as substrate.

Example 13

Conjugation of lipase with Tresyl chloride activated mPEG 15.000

170 mg of Lipalase® in 17 ml of 0.1M borate, 0.8M NaCl, pH 9.2 was incubated with 2.19 g of mPEG 15.000 activated according to Example 2 for 3 hours at ambient temperature. The reaction was stopped by addition of 730 µl 2M Glycine and the derivative purified by size-exclusion chromatography (Spherogel TSK-G2000 SWG).

Relative to the parent Lipolase® the derivative retained some 64% residual enzyme activity using glycerol tributyrate as substrate.

Example 14

Conjugation of lipase with N-succinimidyl carbonate activated mPEG 15.000

100 mg of Lipolase® in 9 ml of 0.1M borate, 1M NaCl, pH 9.2 was incubated with 2.576 g of mPEG-15000 activated with N-succinimidyl carbonate according to Example 3 for 3 hours at ambient temperature. The reaction was stopped by addition of 859 µl 2M Glycine and the derivative purified by size-exclusion chromatography (Spherogel TSK-G2000 SWG).

Relative to the parent Lipolase® the derivative retained some 60% residual enzyme activity using glycerol tributyrate as substrate.

The molecular weight of the obtained conjugate was determined to be about 150 kDa using SDS-PAGE.

Example 15

Carbodiimide mediated conjugation of lipase with mPEG-NH$_2$-5.000

0.4 mg of Lipolase® in 5 ml of 50 mM MES buffer, 0.2M NaCl, pH 5.0 was incubated with 400 mg of mPEG-NH$_2$-5.000, and 125 mg 1-ethyl-3-(3-dimethylaminopropyl) carbodiimide (EDC) for 3 hours at ambient temperature. The derivative was purified by size-exclusion chromatography (Superdex 200, Pharmacia).

Relative to the parent Lipolase® the derivative retained about 1% residual enzyme activity using glycerol tributyrate as substrate.

Example 16

Conjugation of laccase with N-succinimidyl carbonate activated mPEG 15.000

100 mg of *Polyporus pintitus* laccase in 10 ml of 0.1M borate, 0.5M NaCl, pH 9.2 was incubated with 1.155 g of mPEG 15.000 activated with N-succinimidyl carbonate according to Example 3 for 2 hours at ambient temperature. The reaction was stopped by addition of 200 µl 2M Glycine and the derivative purified by size-exclusion chromatography (Superdex 200) and dialysed towards 50 mM borate, pH 9.0.

Molecular weights were determined by SDS-PAGE to be in the range of 150 to 200 kDa.

Relative to the parent Laccase the derivative retained some 55% residual enzyme activity.

Example 17

Conjugation of *Coprinus cinereus* peroxidase with N-succinimidyl carbonate activated mPEG 15.000

75 mg of peroxidase in 7.5 ml of 0.1M borate, 0.5 NaCl, pH 9.2 was incubated with 1.579 g of mPEG 15.000 activated with N-succinimidyl carbonate according to Example 3 for 2 hours at ambient temperature. The reaction was stopped by addition of 200 µl 2M Glycine and the derivative purified by size-exclusion chromatography (Superdex 200) and dialysed towards 0.1M Na-phosphate, pH 7.0.

Molecular weights are determined by SDS-PAGE to be in the range of 150 to 200 kDa.

Relative to the parent peroxidase the derivative retained some 79% residual enzyme activity.

Example 18

Conjugation of cellulase with activated Tresyl chloride activated PEG 5.000

27.2 mg of Carezyme® was incubated in 50 mM NaCarbonate buffer pH 8.5 with 115.2 mg of Tresyl chloride activated PEG 5.000. The reaction was carried out at ambient temperature using magnetic stirring. Reaction time was 1 hour.

The molecular weight of the derivatives (assessed as the relative mobility of denatured proteins in SDS polyacrylamide gels) was 53–63 kDa, corresponding 2–4 moles of PEG attached per mole Carezyme®.

Compared to an internal standard (a highly purified preparation of the parent enzyme), the derivative held 63% residual activity.

Example 19

Conjugation of substrate protected cellulose with activated mPEG 5.000

To shield the active site of the enzyme during mPEG conjugation, the enzyme was diluted in a carboxymethyl cellulose solution (0.5% W/V) to the same final buffer and protein concentration as in Example 3 (4 ml NaCarbonate pH 8.5, 6.8 mg/ml Carezyme® and 115.2 mg of N-succinimidyl carbonate activated mPEG 5.000). The reaction was conducted at 4° C. for 1 hour.

As in Example 18, the degree of derivatization was evaluated by SDS electrophoresis using 4–20% gradient polyacrylamide gels, followed by silver staining. The apparent mass of the derivative was 53–63 kDa, corresponding 2–4 moles of PEG attached per mole Carezyme®.

The catalytic activity of the derivative was 90% of that of the parent enzyme.

Example 20

Conjugation of product stabilized cellulase with activated mPEG 5.000

To protect the active site of Carezyme®, cellobiose (Sigma, C7292) was added to a final concentration of 80 mM, corresponding to a molar excess of 5.000 fold. The conjugation of N-succinimidyl carbonate activated mPEG 5.000 with Carezyme® in the presence of cellobiose, and the characterization of the products, was carried out as described in above. The apparent mass of the derivative was 53–63 kDa, corresponding 2–4 moles of PEG attached per mole Carezyme®. The derivative held 100% residual activity.

Example 21

Conjugation of cellulase with N-succinimidyl carbonate activated mPEG 15.000

20 mg of Carezyme® in 1 ml of 0.1M borate, 1 mM CaCl, pH 10.0, was incubated with 54.3 mg of mPEG 15.000 activated with N-succinimidyl carbonate according to Example 3 for 3 hours at ambient temperature. The reaction was stopped by addition of 18 $\mu$l 2M Glycine and the derivative purified by size-exclusion chromatography (Superdex 200).

Relative to the parent Carezyme® the modified Carezyme® retained some 66% residual enzyme activity.

Example 22

Rat intratrachaeal (IT) trails

Brown Norway rats (BN) was stimulated intratrachaeally (IT) with modified Subtilisin Novo, Lipolase®, *Polyporus pinsitus* laccase and Carezyme®, respectively, all enzymes conjugation with N-succinimidyl carbonate activated mPEG 15.000 as described in the examples above, and the corresponding parent enzymes as controls.

Sera from immunized animals were tested in a specific IgE ELISA (described above) to elucidate whether the molecules had penetrated the lung epithelias and activated the immune response system giving rise to a specific IgE respons (See FIG. 2, 3, 4 and 5).

As can be seen from the figures the response of the rats exposed intratracheally with the modified enzyme is reduced in comparison to rats having been exposed intratracheally with the parent enzymes.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

What is claimed is:

1. A composition comprising (a) a modified protease, wherein said protease is conjugated to a polymer with a molecular weight in the range of 1 kDa to 60 kDa, wherein said modified protease exhibits reduced respiratory allergenicity relative to an unmodified protease and (b) a substance for industrial application which renders the composition unsuitable for pharmaceutical use.

2. A composition as defined in claim 1, wherein said protease is a serine protease.

3. A composition as defined in claim 2, wherein said serine protease is trypsin.

4. A composition as defined in claim 1, wherein said polymer is selected from the group consisting of polyalkylene oxides (PAO), polyvinyl alcohol (PVA), polycarboxylates, poly-(vinylpyrolidone), poly-D,L-amino acids, dextrans, hydrolysates of chitosan, starches, guar gum, pullulan, inulin, xanthan gum, carrageenin, pectin, and alginic acid hydrolysates.

5. A composition as defined in claim 1, wherein said polymer is a polyalkylene oxide selected from the group consisting of polyethylene glycols (PEG), methoxypolyethylene glycols (mPEG) and polypropylene glycols, PEG-glycidyl ethers (Epox-PEG), PEG-oxycarbonylimidazole (CDI-PEG), Star-PEGs, and branched PEGs.

6. A composition as defined in claim 1, wherein said polymer has a molecular weight ($M_r$) between 2 kDa and 35 kDa.

7. A composition as defined in claim 1, wherein said protease is conjugated with from 1 to 25 polymer molecules per molecule of protease.

8. A composition as defined in claim 1, wherein the substance for industrial application is selected from the group consisting of a personal care product, an oral care product, a skin care product, a cosmetic, a contact lenses hygiene product, a detergent, an oral or dermal pharmaceutical, an agrochemical, food or feed, a baking product, a product for processing textiles, and a composition for cleaning hard surfaces.

9. A composition as defined in claim 1, wherein the substance for industrial application is a hair care or hair treatment product.

10. A composition as defined in claim 9, wherein the hair care or hair treatment product is selected from the group consisting of shampoo, balsam, hair conditioners, hair waving compositions, hair dyeing compositions, hair tonic, hair liquid, hair cream, hair rinse, and hair spray.

11. A composition as defined in claim 1, wherein the substance for industrial application is an oral care product selected from the group consisting of dentifrice, mouth washes, and chewing gum.

12. A composition as defined in claim 1, wherein the substance for industrial application is a skin care product selected from the group consisting of skin cream, skin milk, cleansing cream, cleansing lotion, cleansing milk, cold cream, cream soap, nourishing essence, skin lotion, milky lotion, calamine lotion, hand cream, powder soap, transparent soap, sun oil, sun screen, shaving foam, shaving cream, and baby oil.

13. A composition as defined in claim 1, wherein the substance for industrial application is a cosmetic selected from the group consisting of lipstick, lip cream, creamy foundation, face powder, powder eye-shadow, powder, foundation, make-up base, essence powder, and whitening powder.

14. A composition as defined in claim 1, wherein the substance for industrial application is a detergent selected from the group consisting of washing powder, liquid detergent, dishwashing detergent, and soap.

* * * * *